US007863428B2

(12) United States Patent  
Dierynck et al.

(10) Patent No.: US 7,863,428 B2  
(45) Date of Patent: Jan. 4, 2011

(54) FLUOROGENIC ENZYME SUBSTRATES AND METHODS OF PREPARATION

(75) Inventors: Inge Dierynck, Antwerpen (BE); Jan Ludwig Goeman, Sint-Niklaas (BE); Koenraad Lodewijk August Van Acker, Temse (BE); Johan Theo André Van Der Eycken, Ninove (BE)

(73) Assignee: Tibotec BVBA (BE)

( * ) Notice: Subject to any disclaimer, the term of this patent is extended or adjusted under 35 U.S.C. 154(b) by 971 days.

(21) Appl. No.: 10/540,057

(22) PCT Filed: Dec. 26, 2003

(86) PCT No.: PCT/EP03/51105

§ 371 (c)(1),  
(2), (4) Date: Nov. 3, 2006

(87) PCT Pub. No.: WO2004/058787

PCT Pub. Date: Jul. 15, 2004

(65) Prior Publication Data

US 2007/0037234 A1 Feb. 15, 2007

(30) Foreign Application Priority Data

Dec. 27, 2002 (EP) .................................. 02102898

(51) Int. Cl.  
*C07H 15/00* (2006.01)  
*C07H 17/00* (2006.01)  
*C07H 17/02* (2006.01)  
*C07H 15/24* (2006.01)

(52) U.S. Cl. .......................... 536/17.4; 536/8; 536/18.1

(58) Field of Classification Search ....................... None  
See application file for complete search history.

(56) References Cited

U.S. PATENT DOCUMENTS

| 4,159,330 | A | 6/1979 | Doria et al. |
| 5,316,906 | A | 5/1994 | Haugland et al. |
| 5,443,986 | A | 8/1995 | Haughland et al. |

FOREIGN PATENT DOCUMENTS

| EP | 0722937 A | 7/1996 |
| EP | 1081138 A1 | 3/2001 |
| WO | WO 93/04077 | * 3/1993 |
| WO | WO 93/04077 A | 3/1996 |
| WO | WO 02/28841 A | 4/2002 |

OTHER PUBLICATIONS

Bolotin et al., "2-Aryl-4H-3, 1-benzoxazin-4-ones and their analogs. II. Some Reactions of 0-Acylaminobenzamides", Chemical Abstracts, vol. 70, No. 17, 1969, Columbus, Ohio, US; abstract No. XP002257309 & ZH. VSES. KHIM. Obshchest., vol. 13, No. 4, pp. 475-476 (1968).

Patent Abstracts of Japan, vol. 2002, No. 5, May 3, 2002 & JP 2002 030085 A (Asahi Glass Co Ltd., Mitsubishi Pharma Corp.), Jan. 29, 2002 abstract.

Diwu et al., "Spectral Properties and Biological Applications of ELF Enzyme Substrates that yield Fluorescent Precipitates at the Enzymatic Activity Sites", Proceedings of SPIE—The International Society for Optical Engineering 3602 Advances in Fluorescence Sensing Technology IV, 1999, pp. 265-274 (XP008023235).

Diwu et al., Fluorescent Molecular Probes I. The Synthesis and Biological Properties of an ELF beta-Glucuronidase Substrate That Yields Fluorescent Precipitates at the Enzymatic Activity Sites, Tetrahedron, Elsevier Science Publishers, Amsterdam, NL, vol. 53, No. 21, May 26, 1997, pp. 7159-7164 (XP004105695).

Naleway et al., "Synthesis and Use of New Fluorogenic Precipitating Substrates", Tetrahedron Letters, vol. 35, No. 46, Nov. 14, 1994, pp. 8569-8572 (XP002230449).

Zhou et al, "A Fluorogenic Substrate for beta-Glucuronidase: Applications in Fluorometric, Polyacrylamide Gel and Histochemiical Assays", Journal of Biochemical and Biophysical Methods, vol. 33, 1996, pp. 197-205 (XP002230450).

NL 6 409 642 A (American Cyanamid Company), Feb. 21, 1966.

Proceedings of SPIE—The International Society for Optical Engineering—"Advances in Fluorescence Sensing Technology IV", 1999, pp. 265-274 (XP008023235).

International Search Report mailed Nov. 23, 2004 for PCT/EP03/51105.

Coburn et al.; "Potential Salicylamide Antiplaque Agents: in Vitro Antibacterial Activity against *Actinomyces viscosusl* "; *J. Med. Chem.*, 1981; 24:1245-1249.

Deligeorgiev, T.G.; An Improved Method for the Preparation of 2-Aryl-, 2-Hetaryl- and 2-Styrylbenzothiazles; *Dyes and Pigments*, 1990; 12:243-248.

Ishikawa, Eiji; "Enzyme Immunoassay of Insulin by Fluorimetry of the Insulin-glucoamylase Complex"; *J. Biochem.*, 1973; 73(6):1319-1321.

Jacquinet, Jean-Claude; "Syntheses of the methyl glycosides of the repeating units of chondroitin 4- and 6-sulfate"; *Carbohydrate Research*, 1990; 199:153-181.

Jefferson, R.A.; "The GUS reporter gene system"; *Nature*, Dec. 1989; 342:837-838.

Jefferson, Richard A.; "Assaying Chimeric Genes in Plants: The GUS Gene Fusion System"; *Plant Molecular Biology Reporter*, Nov. 1987; 5(4):387-405.

Larison et al.; "Use of a New Fluorogenic Phosphatase Substrate in Immunohistochemical Applications"; *The Journal of Histochemistry and Cytochemistry*, 1995; 43(1):77-83.

Nudelman et al.; "Selective Deacetylation of Anomeric Sugar Acetates with Tin Alkoxides"; *Carbohydrate Research*, 1987; 162:145-152.

(Continued)

*Primary Examiner*—Travis C McIntosh, III

(57) ABSTRACT

This invention relates to hydrolase fluorogenic substrates with improved cell permeability, methods for the preparation thereof, and methods of measuring activities of hydrolases, particularly in cell-based assays. The substrates easily diffuse into the cells, where they are enzymatically processed to yield photostable fluorescent products, and are particularly fitted for visualising enzyme-derived activities in cell-based assays.

5 Claims, 3 Drawing Sheets

OTHER PUBLICATIONS

Figure 1:
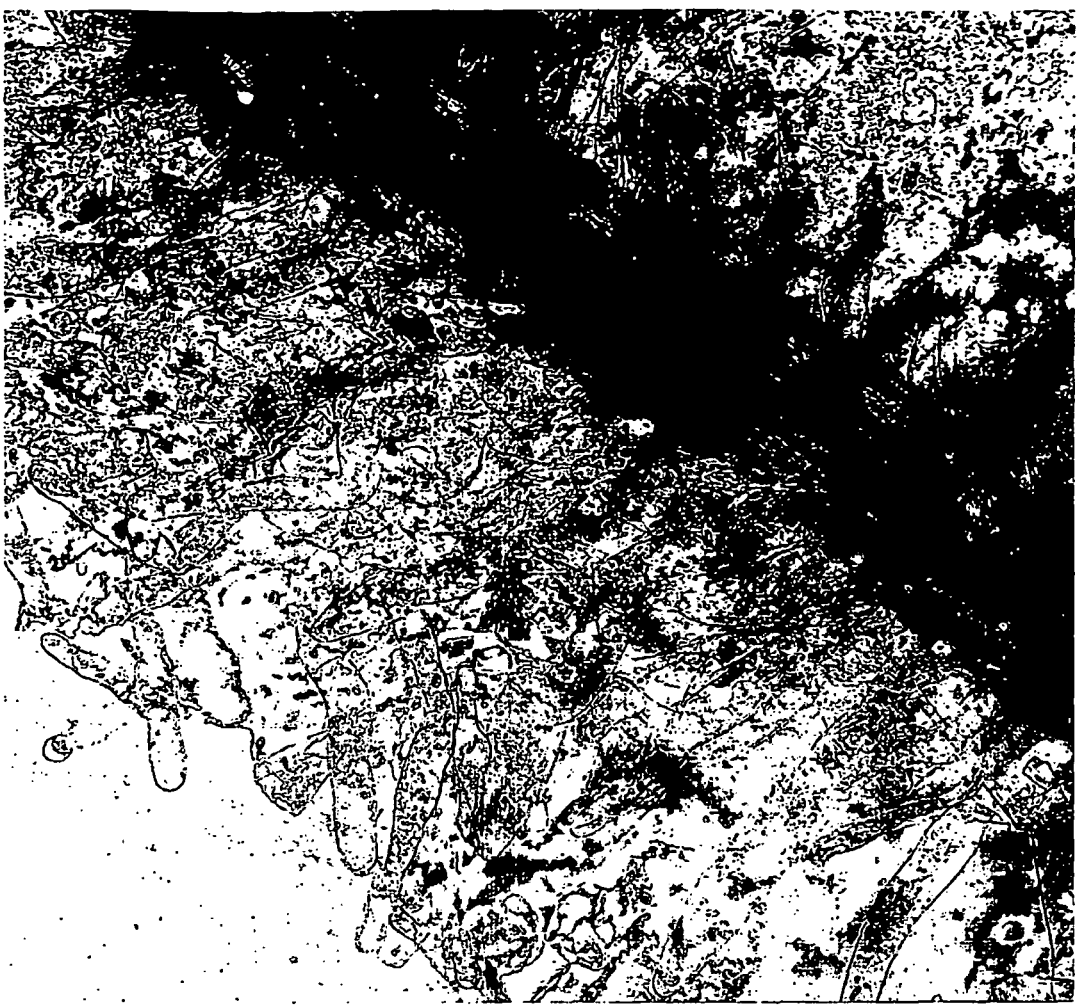

Pater, Richard; "2-Aryl-4(3H)quinazolinones"; *Journal of Heterocyclic Chemistry*, 1971; 8(5):699-702.

Schmidt et al.; "Facile Synthesis of α- and β-O-Glycosyl Imidates; Preparation of Glycosides and Disaccharides"; *Angewandte Chemie, A Journal of the Gesellschaft Deutscher Chemiker*, 1980; 19(9):731-732.

Stille, John K.; "The Palladium-Catalyzed Cross-Coupling Reactions of Organotin Reagents with Organic Electrophiles"; *Angewandte Chemie, A Journal of the Gesellschaft Deutscher Chemiker*, 1986; 25(6):508-524.

Szardenings et al.; "A General and Convenient Synthesis of Novel Phosphotyrosine Mimetics"; *Tetrahedron Letters*, 1996; 37(21):3635-3638.

Urlaub et al.; "Effect of Gamma Rays at the Dihydrofolate Reductase Locus: Deletions and Inversions"; *Somatic Cell and Molecular Genetics*, 1986; 12(6): 555-566.

Vedejs, E.; "Clemmensen Reduction of Ketones in Anhydrous Organic Solvents"; *Organic Reactions*, 1975; 22:401-422.

Zhu et al.; "Activity-Based Fluorescent Probes that Target Phosphatases"; *Tetrahedron Letters*, 2003; 44:2669-2672.

\* cited by examiner

FLUOROGENIC ENZYME SUBSTRATES AND METHODS OF PREPARATION

CROSS REFERENCE TO RELATED APPLICATIONS

This application is the national stage of Application No. PCT/EP03/051105, filed Dec. 26, 2003, which application claims priority from European Patent Application No. EP 02102898.2 filed Dec. 27, 2002.

FIELD OF THE INVENTION

This invention relates to hydrolase fluorogenic substrates with improved cell permeability, methods for the preparation thereof, and methods of measuring activities of hydrolases, particularly in cell-based assays. The substrates easily diffuse into the cells, where they are enzymatically processed to yield photostable fluorescent products, and are particularly fitted for visualising enzyme-derived activities in cell-based assays.

BACKGROUND OF THE INVENTION

For studying cell biology, a number of techniques are available for detecting, measuring, and following almost any chosen molecule in a cell. Light-microscope techniques are vastly used for observing cells. Cells that have been fixed and stained can be studied in a conventional light microscope, while fluorescent dyes coupled to antibodies can be used to locate specific molecules in cells using a fluorescent microscope. The confocal scanning microscope provides thin optical sections and can be used to reconstruct a three-dimensional image. Three-dimensional views of the surfaces of cells and tissues can be obtained by scanning electron microscopy, while the interior of membrane and cells can be visualised by freeze-fracture and freeze-etch electron microscopy, respectively.

The classical methods of microscopy give good views of cell architecture, but they provide little information about cell chemistry. In cell biology it is often important to determine the quantities of specific molecules and to know where they are in the cell and how their level or location changes in response to extracellular or intracellular signals. The molecules of interest range from small inorganic ions, such as $Ca^{2+}$ or $H^+$, to large molecules, such as specific proteins, RNAs, or DNA. Sensitive methods have been developed for assaying each of these types of molecules, as well as for following the dynamic behaviour of many of them in living cells. One particular method is the introduction of probes into living cells in order to monitor the chemical conditions within the cell.

Certain probes interestingly consist of fluorogenic or fluorescent dyes coupled to a blocking group thus forming an enzyme substrate. These probes are cleavable by enzymes, and yield fluorescent dye precipitates, which may be detected by fluorescence microscopy in a highly sensitive fashion.

Amongst different enzyme substrates, hydrolase substrates, i.e. substrates recognized by hydrolases, have been conveniently used in assaying cell biology. Hydrolases are enzymes found in a broad variety of organisms, including bacteria, yeast and higher animals and plants. They act by catalyzing a hydrolysis reaction. Thus, they break down a compound (i.e., the substrate) by cleaving a covalent bond in the compound and inserting a water molecule across the bond. Hydrolase enzymes include those that act on ester bonds, on peptide bonds, on carbon-nitrogen bonds other than peptide bonds, on glycoside bonds, on ether bonds, and on acid anhydrides, among others. Esterases, lipases, peptidases, glycosylases, such as glycosidases, phosphatases, sulfatases, nucleases, exonucleases, endonucleases, are typical exponents of this type of enzymes.

Hydrolases may be used in enzyme labelled fluorescence assays, where the fluorescence mechanism is used to detect enzyme activity. Enzyme labelled fluorescence assays are based on the enzymatic conversion of specific substrates into the corresponding fluorescent precipitates. These substrates may also be refereed to as "fluorogenic substrates" as they are able to be cleaved and yield fluorescent precipitates upon enzymatic action.

As such, certain fluorogenic β-D-glucuronidase or β-D-galactosidase substrates are known. For instance, the use of the β-D-galactosidase (GAL) enzyme and its fluorogenic substrate 4-methylumbelliferyl β-D-galactoside has been cited in the literature as an example (Ishikawa E., Imagawa M., & Hashids S., "*Ultrasensitive Enzyme Immunoassay Using Fluorogenic, Lumenogenic, Radioactive and Related Substrates and Factors to Limit Sensitivity*", J. Biochem 73, 1319-1321, 1973). Also the use of the β-D-glucuronidase (GUS) enzyme and its fluorogenic substrate 4-methylumbelliferyl-β-D-glucuronide has been described (Jefferson R. A. "*Assaying Chimeric Genes in Plants: The GUS Gene Fusion System*", Plant Mol. Biol. Rep. 5, 387-405, 1987; Jefferson R. A. "*The GUS Reporter Gene System*", Nature, 342, 837-838, 1989).

Also fluorogenic substrates that are made from a class of fluorophores, generally including quinazolinones (quinazolones), benzimidazoles, benzothiazoles, benzoxazoles, quinolines, indolines, and phenanthridines, have been described. These substrates can be enzymatically converted to a detectable phenolic product, e.g. formation of a soluble coloured or fluorescent product or formation of a precipitate. For example U.S. Pat. No. 5,316,906 and U.S. Pat. No. 5,433,986 describe this kind of substrates which consist of substances coupled with phosphate, sulfate or sugar groups and which form a highly fluorescent precipitate upon reaction with the appropriate enzyme. Both US patents also mention the use of these fluorogenic substrates to detect and study enzyme activity. Particular examples of this kind of substrates include the ELF97® β-D-galactosidase substrate (ELF97® β-D-galacto-pyranoside) (1) and the ELF97® β-D-glucuronidase substrate (ELF97® β-D-glucuronide) (2) that have been developed and awe commercially available.

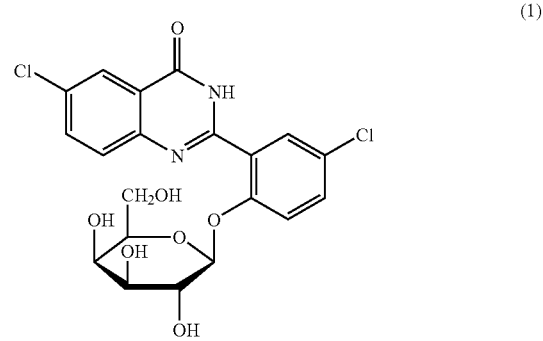

(1)

-continued

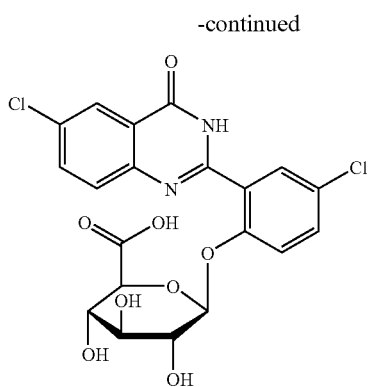

(2)

These ELF97® β-D-galactosidase and ELF97® β-D-glucuronidase substrates are non-fluorescent but can react with GAL or GUS enzymes, respectively, resulting in fluorescent precipitates and non-fluorescent cleaved products.

However, one disadvantage of known fluorogenic substrates is their impermeability for cell membranes. As a consequence, GUS and GAL assays are generally destructive for the cells, i.e. the cell membrane needs to be permeabilized prior to detection of an intracellular analyte, and are therefore not suitable for use under in vivo conditions, or under in vitro conditions where cell integrity is desired. Many other substrates are in contrast not sufficiently photostable, such as fluorescein, which bleaches after a few minutes, loosing the fluorescence necessary for detection.

There exist in the state of the art various methods to introduce a membrane-impermeable substance into a cell. One approach is to micro inject the molecules into the cell through a micropipette. Other approaches consist of partially disrupting the structure of the cell plasma membrane, by using a powerful electric shock or a chemical such as a low concentration of detergent. A third method for introducing large molecules into cells is to cause membranous vesicles containing these molecules to fuse with the cell plasma membrane.

As a consequence, the present invention aims to provide a new approach for introducing a membrane-impermeable fluorogenic substrate into a cell. In particular, it is an object of present invention to provide novel fluorogenic hydrolase substrates, which have an increased permeability for cell membranes without jeopardising their photostability, and which are specifically recognised by specific enzymes.

Further, it is also an object of the present invention to provide methods for preparing the subject fluorogenic hydrolase substrates, substantially free of impurities.

Present invention also aims to provide fluorogenic hydrolase substrates, which can be used in a variety of cellular assays. In particular the subject fluorogenic enzyme substrates can be used in different applications, such as for studying or detecting various characteristics related to enzyme activity, gene expression or promoter activity and specificity.

FIGURES

FIG. 1. Testing substrate (compound 27) in vivo. The picture shows a confocal microscopy view on hair-root cells of a transgenic tobacco plant. The presence of the GUS reporter enzyme in the cell nucleus can be shown with lipophilic GUS substrate (compound 27) without permeabilizing cells.

Figure 2:
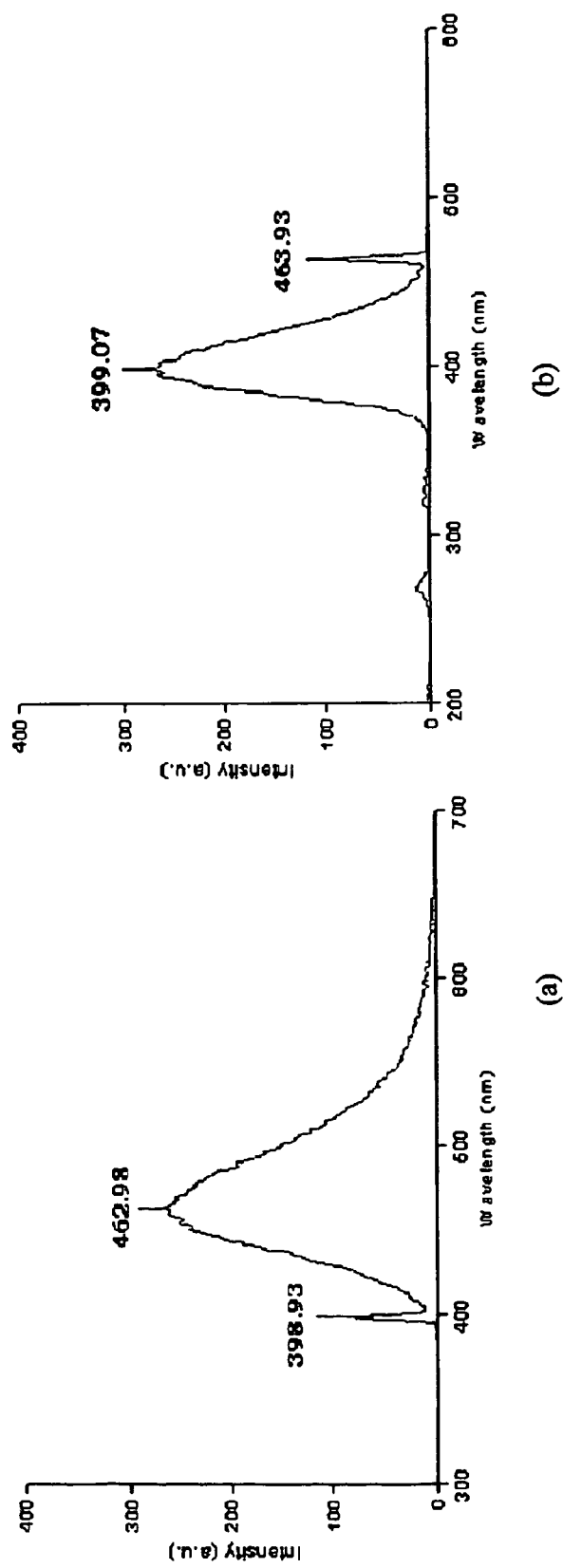

FIG. 2. (a) Emission spectrum of compound 21 at fluorescence maximum.
(b) Excitation spectrum of compound 21 at fluorescence maximum.

Figure 3:

FIG. 3. Fluorescent (=GUS transfected) and non-fluorescent 293T cells with the presence of compound 27.

DETAILED DESCRIPTION OF THE INVENTION

The present invention relates to novel hydrolase substrates and the fluorescent precipitates thereof useful in enzyme labeled fluorescence assays. More particularly, the present invention relates to fluorogenic substituted hydrolase substrates.

These novel fluorogenic substituted hydrolase substrates exhibit improved permeability for cell membranes compared to other known fluorogenic substrates. This particular characteristic allows the enzyme substrates of the present invention to enter into the cytoplasm of a wide variety of cells, facilitating their uptake by all kind of cells. The improved permeability of these substituted enzyme substrates of present invention is surprisingly related to a lipophilic substitution on the fluorophore moiety with a polar side-chains, despite the fact that such substitution leads to the synthesis of larger molecules, and employing different synthesis paths compared to what is comprised in the state of the art.

For instance, substitution of a substrate according to the present invention with one pentyl or two butyl or two pentyl groups on its fluorophore moiety, i.e. the compound considered without the BLOCKING GROUP, can enable the entire molecule, fluorophore plus the BLOCKING GROUP, to enter cells by simple diffusion. In addition, this mono-pentylated, di-butylated or di-pentylated compounds are still good substrates for enzymes such as the GUS enzyme, as a rapid fluorescence emission can be observed after addition of a purified enzyme. Using transient transfection experiments of the GUS reporter gene, it was shown, for instance, that this kind of substrate is indeed membrane permeable and is suitable for the detection of GUS over-expressing cells.

Furthermore, the substrates of the present invention yield photostable fluorescent products without requiring the addition of colour-developing or precipitating reagents. These soluble enzyme substrates yield fluorescent precipitates upon enzymatic hydrolysis without compromising the enzymatic activity. Furthermore, the novel enzyme substrates of the present invention, upon cleavage and precipitation, form small crystals, and are therefore suited for detailed image analysis and visualization.

The present invention relates as well to a method for preparing the subject fluorogenic substituted hydrolase substrates. More particularly, present invention concerns specific methods for the preparation of fluorogenic substituted enzyme substrates of high purity.

Methods for measuring activities of enzymes in cell-based assays are also comprised in the present invention. A particular application of the enzyme substrates is the visualization of gene expression or promoter activity and specificity in cell-based assays. Further scope of the applicability of the present invention will become apparent from the detailed description provided below. It should be understood, however, that the following detailed description and examples, while indicating preferred embodiments of the invention, are given by way of illustration only, since various changes and modifications within the spirit and scope of the invention will become apparent to those skilled in the art from the following description.

In one embodiment, the present invention relates to novel fluorogenic substituted hydrolase substrates represented by the general formula (I):

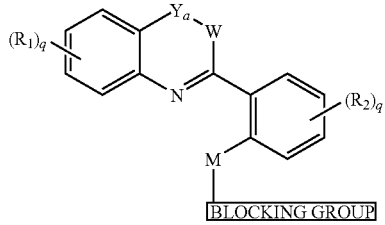

and biologically acceptable salts, or pro-reporter molecules (such as esters, lower alkyl ester precursors, e.g. acetates, methyl ester forms) thereof;

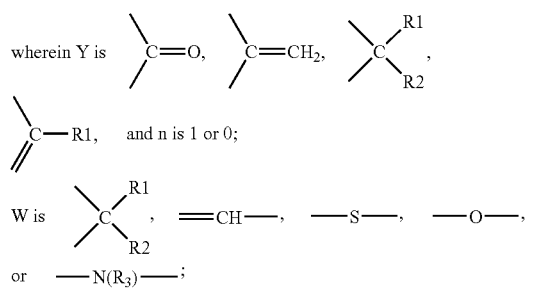

M is oxygen, nitrogen or sulfur;

$R_1$ and $R_2$ are the same or different and are, each independently, hydrogen, halogen, nitro, azido, mercapto, sulfeno, sulfino, sulfo, cyano, amino, $R_4-$, $R_4O-$, $R_4(C=Z)-$, $R_4X-C(=Z)-$, $R_4-C(=Z)-X-$, $R_4X-C(=Z)-Q-$, $R_4S-$, $R_4-S(=O)-$, $R_4-S(=O)-O-$, $R_4-S(=O)_2-O-$, $R_4O-S-$, $R_4O-S(=O)-$, $R_4O-S(=O)_2-$, $R_4R_5N-S(=O)-$, $R_4R_5N-S(=O)_2-$, $R_4R_5N-$, $[R_4-C(=Z)][R_5]N-$, $[R_4-C(=Z)][R_5C(=X)]N-$, $R_4R_5N-C(=Z)-$, $R_4R_5N-C(=Z)-X-$, $[R_4R_5N-C(=Z)]R_6N-$, $[R_6N-C(=Z)][R_6-C(=X)]N-$, $[R_4S(=O)][R_5]N-$, $[R_4-S(=O)_2][R_5]N-$, $(R_4X)(R_5Q)P(=Z)-$, $(R_4R_5N)(R_6X)P(=Z)-$, $(R_4R_5N)(R_6R_7N)P(=Z)-$, $(R_4X)(R_5Q)P(=Z)-O-$, $(R_4R_5N)(R_6X)P(=Z)-O-$, $(R_4R_5N)(R_6R_7N)P(=Z)-O-$, $(R_4X)(R_5Q)P(=Z)-S-$, $(R_4R_5N)(R_6X)P(=Z)-S-$, $(R_4R_5N)(R_6R_7N)P(=Z)-S-$, $[(R_4X)(R_5Q)P(=Z)][R_6]N-$, $[(R_4R_5N)(R_6X)P(=Z)][R_7]N-$, $[(R_4R_5N)(R_6R_7N)P(=Z)][R_8]N-$, $(R_4)(R_5X)P(=Z)-O-$, $(R_4)(R_5R_6N)P(=Z)-O-$, $(R_4)(R_5X)P(=Z)-S-$, $(R_4)(R_5R_6N)P(=Z)-S-$, $[(R_4)(R_5X)P(=Z)][R_6]N-$, $[(R_4)(R_5R_6N)P(=Z)][R_7]N-$;

wherein X, Z and Q are the same or different and are each independently oxygen or sulfur;

wherein $R_3$ is $R_4$, $R_4-C(=Z)-$, $R_4X-C(=Z)$, $R_4R_5N-C(=Z)-$, $R_4O-S(=O)-$, $R_4O-S(=O)_2-$, $R_4R_5N-S(=O)-$, $R_4R_5N-S(=O)_2-$, $(R_4X)(R_5Q)P(=Z)-$, $(R_4R_5N)(R_6X)P(=Z)-$, $(R_4R_5N)(R_6R_7N)P(=Z)-$;

wherein $R_4$, $R_5$, $R_6$, $R_7$ and $R_8$ are the same or different and are each independently hydrogen, $C_{1-8}$alkyl, $C_{2-8}$alkenyl, $C_{2-8}$alkynyl, $C_{3-7}$cycloalkyl aryl, Het[1], Het[2];

wherein each q is the same or different and each independently equal to 0, 1, 2, 3, or 4;

wherein any $C_{1-8}$alkyl, $C_{2-8}$alkenyl, $C_{2-8}$alkynyl or amino group, may be further mono, di-, or tri-substituted (if the valency allows it) with $C_{1-4}$alkoxy, $C_{1-4}$alkylcarbonyl, $C_{1-4}$alkoxycarbonyl, $C_{1-4}$alkylthio, $C_{1-4}$alkylsulfenyl, $C_{1-4}$alkylsulfinyl, $C_{1-4}$alkylsulfonyl, $C_{1-4}$alkylamino, halogen, nitro, azido, mercapto, sulfeno, sulfino, sulfo, cyano, amino, aryl, Het[1] or Het[2] substituents;

with the proviso that at least one $R_1$, $R_2$ or $R_3$ is a moiety with at least 4 carbons.

In another embodiment, present invention relates to novel fluorogenic substituted hydrolase substrates represented by the general formula (I):

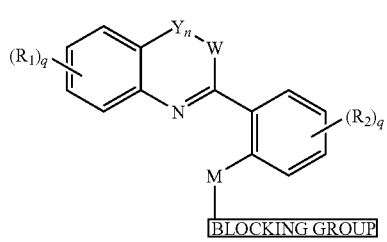

and biologically acceptable salts, and pro-reporter molecules thereof;

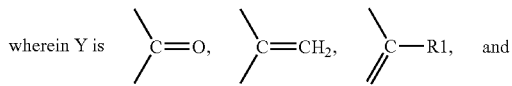

n is 1 or 0;

W is $=CH-$, $-S-$, $-O-$, or $-N(R_3)-$;

M is oxygen, nitrogen or sulfur;

$R_1$ and $R_2$ are, each independently, hydrogen, halogen, nitro, azido, mercapto, sulfeno, sulfino, sulfo, cyano, amino, $R_4-$, $R_4O-$, $R_4C(=Z)-$, $R_4X-C(=Z)-$, $R_4-C(=Z)-X-$, $R_4X-C(=Z)-Q-$, $R_4S-$, $R_4-S(=O)-$, $R_4-S(=O)-O-$, $R_4-S(=O)_2-O-$, $R_4O-S(=O)-$, $R_4O-S(=O)_2-$, $R_4R_5N-S(=O)-$, $R_4R_5N-S(=O)_2-$, $R_4R_5N-$, $[R_4-C(=Z)][R_5]N-$, $[R_4-C(=Z)][R_5-C(=X)]N-$, $R_4R_5N-C(=Z)-$, $R_4R_5N-C(=Z)-X-$, $[R_4R_5N-C(=Z)][R_6]N-$, $[R_4R_5N-C(=Z)][R_6-C(=X)]N-$, $[R_4-S(=O)][R_5]N-$, $[R_4-S(=O)_2][R_5]N-$, $(R_4X)(R_5Q)P(=Z)-$, $(R_4R_5N)(R_6X)P(=Z)-$, $(R_4R_5N)(R_6R_7N)P(=Z)-$, $(R_4X)(R_5Q)P(=Z)-O-$, $(R_4R_5N)(R_6X)P(=Z)-O-$, $(R_4R_5N)(R_6R_7N)P(=Z)-O-$, $(R_4X)(R_5Q)P(=Z)-S-$, $(R_4R_5N)(R_6X)P(=Z)-S-$, $(R_4R_5N)(R_6R_7N)P(=Z)-S-$, $[(R_4X)(R_5Q)P(=Z)][R_6]N-$, $[(R_4R_5N)(R_6X)P(=Z)][R_7]N-$, $[(R_4R_5N)(R_6R_7N)P(=Z)][R_8]N-$, $(R_4)(R_5X)P(=Z)-O-$, $(R_4)(R_5R_6N)P(=Z)-O-$, $(R_4)(R_5X)P(=Z)-S-$, $(R_4)(R_5R_6N)P(=Z)-S-$, $[(R_4)(R_5X)P(=Z)][R_6]N-$, $[(R_4)(R_5R_6N)P(=Z)][R_7]N-$;

wherein X, Z and Q are, each independently, oxygen or sulfur;

$R_3$ is $R_4$, $R_4-C(=Z)-$, $R_4X-C(=Z)-$, $R_4R_5N-C(=Z)-$, $R_4O-S(=O)-$, $R_4O-S(=O)_2-$, $R_4R_5N-S$ (=O)—, $R_4R_5N$—$S(=O)_2$—, $(R_4X)(R_5Q)P(=Z)$—, $(R_4R_5N)(R_6X)P(=Z)$—, $(R_4R_5N)(R_6R_7N)P(=Z)$—;

wherein $R_4$, $R_5$, $R_6$, $R_7$ and $R_8$ are, each independently, hydrogen, $C_{1-8}$alkyl, $C_{2-8}$alkenyl, $C_{2-8}$alkynyl, $C_{3-7}$cycloalkyl, aryl, $Het^1$, $Het^2$;

each q is independently 0, 1, 2, 3, or 4;

wherein any $C_{1-8}$alkyl, $C_{2-8}$alkenyl, $C_{2-8}$alkynyl or amino group, may be further mono, di-, or tri-substituted (if the valency allows it) with $C_{1-4}$alkoxy, $C_{1-4}$alkylcarbonyl, $C_{1-4}$alkoxycarbonyl, $C_{1-4}$alkylthio, $C_{1-4}$alkylsulfenyl, $C_{1-4}$alkylsulfinyl, $C_{1-4}$alkylsulfonyl, $C_{1-4}$alkylamino, halogen, nitro, azido, mercapto, sulfeno, sulfino, sulfo, cyano, amino, aryl, $Het^1$ or $Het^2$ substituents;

wherein the BLOCKING GROUP is a mono- or polysaccharide derivate, phosphate derivate, or sulfate derivate;

with the proviso that at least one $R_1$, $R_2$ and $R_3$ is a moiety with at least 4 carbons.

In an embodiment, the present invention relates to novel compounds represented by the general formula (I) which are fluorogenic substituted hydrolase substrates:

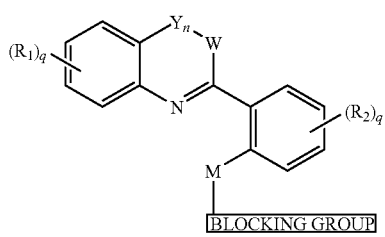

(I)

and biologically acceptable salts thereof;

wherein Y is C=O, C=CH$_2$, C—R1, and n is 1 or 0;

W is =CH—, —S—, —O—, or —N(R$_3$)—;

M is —O—, —N(R$_3$)—, or —S—;

each $R_1$ and each $R_2$ present in formula (I) are, independently, hydrogen, halogen, nitro, azido, mercapto, sulfeno, sulfino, sulfo, cyano, amino, $R_4$—, $R_4O$—, $R_4$—C(=Z)—, $R_4X$—C(=Z)—, $R_4$—C(=Z)—X—, $R_4X$—C(=Z)-Q-, $R_4S$—, $R_4$—S(=O)—, $R_4$—S(=O)$_2$—, $R_4$—S(=O)—O—, $R_4$—S(=O)$_2$—O—, $R_4O$—S—, $R_4O$—S(=O)—, $R_4O$—S(=O)$_2$—, $R_4R_5N$—S(=O)—, $R_4R_5N$—S(=O)$_2$—, $R_4R_5N$—, [$R_4$—C(=Z)][$R_5$]N—, [$R_4$—C(=Z)][$R_5$—C(=X)]N—, [$R_4X$—C(=Z)][$R_5$]N—, [$R_4X$—C(=Z)][$R_5$—C(=Q)]N—, $R_4R_5N$—C(=Z)—, $R_4R_5N$—C(=Z)—X—, [$R_4R_5N$—C(=Z)][$R_6$]N—, [$R_4R_5N$—C(=Z)][$R_6C$(=X)]N—, [$R_4$—S(=O)][$R_5$]N—, [$R_4$—S(=O)$_2$][$R_5$]N—, $(R_4X)(R_5Q)P(=Z)$—, $(R_4R_5N)(R_6X)P(=Z)$—, $(R_4R_5N)(R_6R_7N)P(=Z)$—, $(R_4X)(R_5Q)P(=Z)$—O—, $(R_4R_5N)(R_6X)P(=Z)$—O—, $(R_4R_5N)(R_6R_7N)P(=Z)$—O—, $(R_4X)(R_5Q)P(=Z)$—S—, $(R_4R_5N)(R_6X)P(=Z)$—S—, $(R_4R_5N)(R_6R_7N)P(=Z)$—S—, [$(R_4X)(R_5Q)P(=Z)][R_6]N$—, [$(R_4R_5N)(R_6X)P(=Z)][R_7]N$—, [$(R_4R_5N)(R_6R_7N)P(=Z)][R_8]N$—, $(R_4)(R_5X)P(=Z)$—O—, $(R_4)(R_5R_6N)P(=Z)$—O—, $(R_4)(R_5X)P(=Z)$—S—, $(R_4)(R_5R_6N)P(=Z)$—S—, [$(R_4)(R_5X)P(=Z)][R_6]N$—, [$(R_4)(R_5R_6N)P(=Z)][R_7]N$—;

wherein X, Z and Q are each, independently, O or S;

$R_3$ is $R_4$, $R_4$—C(=Z)—, $R_4X$—C(=Z)—, $R_4R_5N$—C(=Z)—, $R_4O$—S(=O)—, $R_4O$—S(=O)$_2$—, $R_4R_5N$—S(=O)—, $R_4R_5N$—S(=O)$_2$—, $(R_4X)(R_5Q)P(=Z)$—, $(R_4R_5N)(R_6X)P(=Z)$—, $(R_4R_5N)(R_6R_7N)P(=Z)$—;

wherein $R_4$, $R_5$, $R_6$, $R_7$ and $R_8$ are each, independently, hydrogen, $C_{1-8}$alkyl, $C_{2-8}$alkenyl, $C_{2-8}$alkynyl, $C_{3-7}$cycloalkyl, aryl, $Het^1$, $Het^2$;

each q present in formula (I) is, independently, 0, 1, 2, 3, or 4;

wherein any $C_{1-8}$-alkyl, $C_{2-8}$alkenyl, $C_{2-8}$alkynyl or amino group, may be further mono, di-, or tri-substituted (if the valency allows it) with $C_{1-4}$alkoxy, $C_{1-4}$alkylcarbonyl, $C_{1-4}$alkoxycarbonyl, $C_{1-4}$alkylthio, $C_{1-4}$alkylsulfenyl, $C_{1-4}$alkylsulfinyl, $C_{1-4}$alkylsulfonyl, $C_{1-4}$alkylamino, halogen, nitro, azido, mercapto, sulfeno, sulfino, sulfo, cyano, amino, aryl, $Het^1$ or $Het^2$ substituents;

wherein the BLOCKING GROUP is a mono- or polysaccharide derivate, phosphate derivate, sulfate derivate, carboxylic acid derivate, or oligopeptide derivate;

with the proviso that at least one of $R_1$, $R_2$ and $R_3$ is $C_{4-8}$alkyl, $C_{4-8}$alkenyl, or $C_{4-8}$alkynyl.

Interestingly, the present invention relates to the fluorogenic substituted hydrolase substrates wherein W is —N—(R3)-, Y is —C(=O), and n is 1 and having the formula (II) and biologically acceptable salts, and pro-reporter molecules thereof;

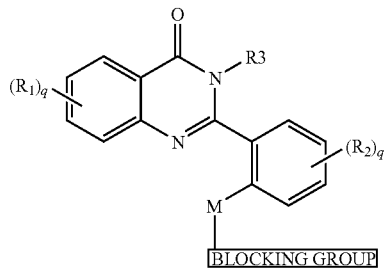

(II)

wherein M, $R_1$, $R_2$, $R_3$, q and the BLOCKING GROUP are as defined as in formula (I).

As well interestingly, the enzyme substrates of the present invention have the formula (III) and biologically acceptable salts, and pro-reporter molecules thereof;

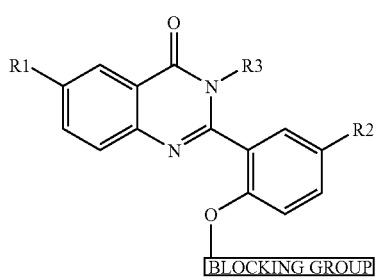

(III)

wherein $R_1$, $R_2$, $R_3$, and the BLOCKING GROUP are as defined as in formula (I).

Preferably, the fluorogenic substituted hydrolase substrates according to the invention have the formula (III) wherein at least one of $R_1$, $R_2$ and $R_3$ is independently chosen from the group consisting of straight and branched butyl, pentyl, hexyl, heptyl, octyl.

More preferably, the fluorogenic hydrolase substrates according to the invention have the formula (III) wherein $R_1$ and $R_2$ are both butyl substituents. Also preferably, the enzyme substrates according to the invention have the formula (III) wherein $R_1$ and $R_2$ are both pentyl substituents. As well preferably, the fluorogenic substituted hydrolase substrates according to the invention have the formula (III) wherein only one of $R_1$ and $R_2$ is a butyl substituent, or a pentyl substituent.

Especially, the present invention relates to a fluorescent precipitate which can be obtained by cleavage of the BLOCKING GROUP from formula (I), by action of a specific enzyme and which results in a fluorescent precipitate having formula (IV):

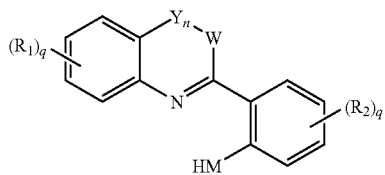

(IV)

wherein Y, n, W, M, $R_1$, $R_2$ and q are as defined as in formula (I).

In another embodiment, the present invention relates to novel compounds represented by the general formula (V) which are fluorogenic substituted hydrolase substrates:

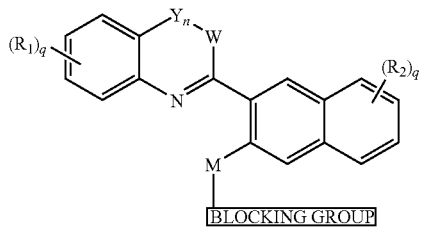

(V)

and biologically acceptable salts, and pro-reporter molecules thereof;

wherein Y is $\diagdown C=O$, $\diagdown C=CH_2$, $\diagdown C-R1$, and n is 1 or 0;

W is =CH—, —S—, —O—, or —N($R_3$)—;

M is —O—, —N($R_3$)—, or —S—;

each $R_1$ and each $R_2$ present in formula (V) are, independently, hydrogen, halogen, nitro, azido, mercapto, sulfeno, sulfino, sulfo, cyano, amino, $R_4$—, $R_4O$—, $R_4$—C(=Z)—, $R_4X$—C(=Z)—, $R_4$—C(=Z)—X—, $R_4X$—C(=Z)-Q-, $R_4S$—, $R_4$—S(=O)—, $R_4$—S(=O)$_2$—, $R_4$—S(=O)—O—, $R_4$—S(=O)$_2$—O—, $R_4O$—S—, $R_4O$—S(=O)—, $R_4O$—S(=O)$_2$—, $R_4R_5N$—S(=O)—, $R_4R_5N$—S(=O)$_2$—, $R_4R_5N$—, [$R_4$—C(=Z)][$R_5$]N—, [$R_4$—C(=Z)][$R_5$—C(=X)]N—, [$R_4X$—C(=Z)][$R_5$]N—, [$R_4X$—C(=Z)][$R_5$—C(=Q)]N—, $R_4R_5N$—C(=Z)—, $R_4R_5N$—C(=Z)—X—, [$R_4R_5N$—C(=Z)][$R_6$]N—, [$R_4R_5N$—C(=Z)][$R_6C$(=X)]N—, [$R_4$—S(=O)][$R_5$]N—, [$R_4$—S(=O)$_2$][$R_5$]N—, ($R_4X$)($R_5Q$)P(=Z)—, ($R_4R_5N$)($R_6X$)P(=Z)—, ($R_4R_5N$)($R_6R_7N$)P(=Z)—, ($R_4X$)($R_5Q$)P(=Z)—O—, ($R_4R_5N$)($R_6X$)P(=Z)—O—, ($R_4R_5N$)($R_6R_7N$)P(=Z)—O—, ($R_4X$)($R_5Q$)P(=Z)—S—, ($R_4R_5N$)($R_6X$)P(=Z)—S—($R_4R_5N$)($R_6R_7N$)P(=Z)—S—, [($R_4X$)($R_5Q$)P(=Z)][$R_6$]N—, [($R_4R_5N$)($R_6X$)P(=Z)][$R_7$]N—, [($R_4R_5N$)($R_6R_7N$)P(=Z)][$R_8$]N—, ($R_4$)($R_5X$)P(=Z)—O—, ($R_4$)($R_5R_6N$)P(=Z)—O—, ($R_4$)($R_5X$)P(=Z)—S—, ($R_4$)($R_5R_6N$)P(=Z)—S—, [($R_4$)($R_5X$)P(=Z)][$R_6$]N—, [($R_4$)($R_5R_6N$)P(=Z)][$R_7$]N—;

wherein the $R_2$ substituent can replace one or more hydrogens on any carbon atom of the naphtyl group, such as carbon atoms C1, C4, C5, C6, C7, and C8, provided that the carbon's valency is not exceeded;

wherein X, Z and Q are each, independently, O or S;

$R_3$ is $R_4$, $R_4$—C(=Z)—, $R_4X$—C(=Z)—, $R_4R_5N$—C(=Z)—, $R_4O$—S(=O)—, $R_4O$—S(=O)$_2$—, $R_4R_5N$—S(=O)—, $R_4R_5N$—S(=O)$_2$—, ($R_4X$)($R_5Q$)P(=Z)—, ($R_4R_5N$)($R_6X$)P(=Z)—, ($R_4R_5N$)($R_6R_7N$)P(=Z)—;

wherein $R_4$, $R_5$, $R_6$, $R_7$ and $R_8$ are each, independently, hydrogen, $C_{1-8}$alkyl, $C_{2-8}$alkenyl, $C_{2-8}$alkynyl, $C_{3-7}$cycloalkyl, aryl, Het$^1$, Het$^2$;

each q present in formula (V) is, independently, 0, 1, 2, 3, or 4;

wherein any $C_{1-8}$alkyl, $C_{2-8}$alkenyl, $C_{2-8}$alkynyl or amino group, may be further mono, di-, or tri-substituted (if the valency allows it) with $C_{1-4}$alkoxy, $C_{1-4}$alkylcarbonyl, $C_{1-4}$alkoxycarbonyl, $C_{1-4}$alkylthio, $C_{1-4}$alkylsulfenyl, $C_{1-4}$alkylsulfinyl, $C_{1-4}$alkylsulfonyl, $C_{1-4}$alkylamino, halogen, nitro, azido, mercapto, sulfeno, sulfino, sulfo, cyano, amino, aryl, Het$^1$ or Het$^2$ substituents;

wherein the BLOCKING GROUP is a mono- or polysaccharide derivate, phosphate derivate, sulfate derivate, carboxylic acid derivate, or oligopeptide derivate;

with the proviso that at least one of $R_1$, $R_2$ or $R_3$ is $C_{4-8}$alkyl, $C_{4-8}$alkenyl, or $C_{4-8}$alkynyl.

The present invention relates as well to a fluorescent precipitate which can be obtained by cleavage of the BLOCKING GROUP from formula (V), by action of a specific enzyme and which results in a fluorescent precipitate having formula (VI):

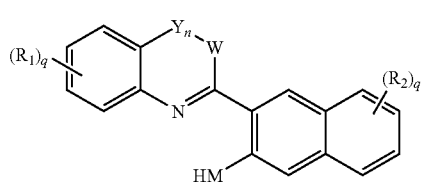

(VI)

wherein Y, n, W, M, $R_1$, $R_2$ and q are as defined as in formula (V).

In general, when W is —N—($R_3$)— and Y is —C(=O)—, the compounds are quinazolinones, also referred to as quinazolones. When W is —N—($R_3$)— and n is 0, the products are benzimidazoles, when W is —O— and n is 0 the products are benzoxazoles, when W is —S— and n is 0 the products are benzothiazoles. When W is =CH— and Y is —C($R_1$)= the compounds are quinolines. When W is =CH— and n is 0, the compounds are indoles. Quinazolinones, benzimidazoles, benzoxazoles, benzothiazoles, quinolines and indoles are all preferred embodiments of the present invention.

Whenever the term "substituted" is used in defining the compounds of formula (I), (II), (III), (IV), (V) or (VI), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, methyl, ethyl, isopropyl, butyl and 2-methyl-propyl and the like.

The term "$C_{1-8}$alkyl" as a group or part of a group defines straight and branched chained saturated hydrocarbon radicals having from 1 to 8 carbon atoms, such as, methyl, ethyl, isopropyl, butyl, 2-methyl-propyl, pentyl, isopentyl, hexyl, heptyl, octyl and the like.

The term "$C_{4-8}$alkyl" as a group or part of a group defines straight and branched chained saturated hydrocarbon radicals having from 4 to 8 carbon atoms, such as, butyl, 2-methyl-propyl, pentyl, isopentyl, hexyl, heptyl, octyl and the like.

The term "$C_{2-8}$alkenyl" as a group or part of a group defines straight and branched chained hydrocarbon radicals having from 2 to 8 carbon atoms containing at least one double bond such as, ethenyl, propenyl, butenyl, pentenyl, pentadienyl, hexenyl, heptenyl, octenyl, and the like.

The term "$C_{4-8}$alkenyl" as a group or part of a group defines straight and branched chained hydrocarbon radicals having from 4 to 8 carbon atoms containing at least one double bond such as butenyl, pentenyl, pentadienyl, hexenyl, heptenyl, octenyl, and the like.

The term "$C_{2-8}$alkynyl" as a group or part of a group defines straight and branched chained hydrocarbon radicals having from 2 to 8 carbon atoms containing at least one triple bond such as, ethynyl, propynyl, butynyl, pentynyl, hexynyl, heptynyl, octynyl, and the like.

The term "$C_{4-8}$alkynyl" as a group or part of a group defines straight and branched chained hydrocarbon radicals having from 4 to 8 carbon atoms containing at least one triple bond such as butynyl, butadiynyl, pentynyl, hexynyl, heptynyl, octynyl, and the like. The term "$C_{4-8}$alkynyl" also encompasses straight and branched chained hydrocarbon radicals having from 4 to 8 carbon atoms containing at least one triple bond and at least one double bond such as 3-hexen-1-ynyl, 2-hepten-4-ynyl, and the like.

The term "$C_{3-7}$cycloalkyl" as a group or part of a group is generic to cyclopropyl, cyclobutyl, cyclopentyl, cyclohexyl or cycloheptyl.

The term "aryl" as a group or part of a group is meant to include mono-, bi, and tricyclic aromatic carbocycles such as phenyl and naphtyl.

The term "$Het^1$" as a group or part of a group is defined as a saturated or partially unsaturated monocyclic, bicyclic or tricyclic heterocycle having preferably 3 to 14 ring members, more preferably 5 to 10 ring members and more preferably 5 to 8 ring members, which contains one or more heteroatom ring members selected from nitrogen, oxygen or sulfur.

The term "$Het^2$" as a group or part of a group is defined as an aromatic monocyclic, bicyclic or tricyclic heterocycle having preferably 5 to 14 ring members, more preferably 5 to 10 ring members and more preferably 5 to 6 ring members, which contains one or more heteroatom ring members selected from nitrogen, oxygen or sulfur.

The substituents $R_1$ and $R_2$ may be attached at any carbon position in the rings of formula (I), (II), (III), (IV), (V) or (VI), as long as their valency allows it.

When any variable (e.g. halogen, $C_{1-8}$alkyl, $C_{4-8}$alkyl) occurs more than one time in any constituent, each definition is independent.

The term "pro-reporter molecules" as used throughout this text means derivatives such as esters, amides and phosphates, such that the resulting in vitro or in vivo biotransformation product of the derivative is the fluorogenic substituted hydrolase substrate as defined in the compounds of formula (I), (II), (III), or (V). Pro-reporter molecules of the present invention are prepared by modifying functional groups present in the compound in such a way that the modifications are cleaved, either by routine manipulation, in vitro or in vivo, to the compounds of formula (I), (II), (III), or (V). The term "pro-reporter molecules" is not to be confused with the BLOCKING GROUP. The pro-reporter molecule will be cleaved to lead to the compounds of formula (I), (II), (III), or (V), encompassing the BLOCKING GROUP and the remainder of the substrate molecule, which molecules of formula (I), (II), (III), or (V), will also be subsequently cleaved by the enzyme of interest to lead to a visible precipitate, corresponding to the remainder of the substrate molecule, i.e. compounds of formula (IV) and (VI).

In one embodiment, the fluorogenic substituted hydrolase substrates according to the invention have the formula (I) wherein at least one of $R_1$, $R_2$ and $R_3$ is independently chosen from the group consisting of straight and branched butyl, pentyl, hexyl, heptyl, octyl.

In another embodiment, the fluorogenic hydrolase substrates according to the invention have the formula (I) wherein $R_1$ and $R_2$ are both butyl substituents. In yet another embodiment, the enzyme substrates according to the invention have the formula (I) wherein $R_1$ and $R_2$ are both pentyl substituents. As well in another embodiment, the fluorogenic substituted hydrolase substrates according to the invention have the formula (I) wherein only one of $R_1$ and $R_2$ is a butyl substituent, or a pentyl substituent.

In one embodiment, the fluorogenic substituted hydrolase substrates according to the invention have the formula (V) wherein at least one of $R_1$, $R_2$ and $R_3$ is independently chosen from the group consisting of straight and branched butyl, pentyl, hexyl, heptyl, octyl.

In another embodiment, the fluorogenic hydrolase substrates according to the invention have the formula (V) wherein $R_1$ and $R_2$ are both butyl substituents. In yet another embodiment, the enzyme substrates according to the invention have the formula (V) wherein $R_1$ and $R_2$ are both pentyl substituents. As well in another embodiment, the fluorogenic substituted hydrolase substrates according to the invention have the formula (I) wherein only one of $R_1$ and $R_2$ is a butyl substituent, or a pentyl substituent.

Particularly, the present invention relates to an enzyme substrate that is able to be cleaved by an enzyme and that has the formula (I), (II), (III) and (V).

Preferably, the fluorogenic substituted hydrolase substrates according to the invention have the formula (III)

wherein at least one of $R_1$, $R_2$ and $R_3$ is independently chosen from the group consisting of straight and branched butyl, pentyl, hexyl, heptyl, octyl.

More preferably, the fluorogenic hydrolase substrates according to the invention have the formula (III) wherein $R_1$ and $R_2$ are both butyl substituents. Also preferably, the enzyme substrates according to the invention have the formula (III) wherein $R_1$ and $R_2$ are both pentyl substituents. As well preferably, the fluorogenic substituted hydrolase substrates according to the invention have the formula (III) wherein only one of $R_1$ and $R_2$ is a butyl substituent, or a pentyl substituent.

"Fluorescence" is the property by which a molecule that is excited by light of a given wavelength emits light at a longer wavelength. Fluorescence is a phenomenon that results from the interaction of a fluorophore with an incident photon. This process is referred to as excitation. Absorption of the photon causes an electron in the fluorophore to rise from its ground state to a higher energy level. Then, the electron reverts to its original level, releasing a photon. This process is referred to as fluorescence emission. The fluorophore then emits light at a longer wavelength than that of the absorbed photon. This is simply because the energy of the emitted photon is lower than that of the absorbed photon, due to energy dissipation during the excited state lifetime.

A "fluorophore" is a molecule that fluoresces, as ft can absorb incident light and in response emits light at a different wavelength.

A "substrate" is defined as a compound or a substance, which is transformed to another substance during a chemical reaction catalyzed by an enzyme or a catalyst.

In the context of the present invention, "fluorogenic substrate" refers to the substrate that can be cleaved into a fluorescent precipitate and a non-fluorescent product upon action of a specific enzyme.

The "BLOCKING GROUP" is defined as a group that changes the excitation or emission properties of the fluorophore, i.e. absorbance or fluorescence. Said change of light activity occurs when the BLOCKING GROUP is cleaved from the remainder of the substrate molecule at the bond between the M moiety and the BLOCKING GROUP by action of a specific hydrolase enzyme. When the BLOCKING GROUP is separated, the resulting group or the remainder of the substrate molecule, results in a visible precipitate. Examples of BLOCKING GROUPS include preferably mono- or polysaccharide derivates, phosphate or sulfate derivates; more preferably derivates of α-D-glucose, β-D-glucose, α-D-galactose, β-D-galactose, α-D-mannose, β-D-mannose, β-D-N-acetyl-glucosamine, β-D-glucuronic acid, β-D-fucose, α-L-fucose, α-L-iduronic acid, β-D-cellobiose, α-L-arabinose, β-D-xylose, α-D-N-acetyl-neuraminic acid (sialic acid), aryl esters of p-guanidino benzoic acid, aryl or alkyl phosphate monoesters, aryl sulfate monoesters, aryl phosphates; even more preferably β-D-galactose and β-D-glucuronic acid derivates. The BLOCKING GROUP moiety of formulas (I), (II), (III), and (V) is selected to be specific for an enzyme of interest. Particularly, the BLOCKING GROUP is a monovalent moiety derived by removal of the anomeric hydroxy group from a mono- or polysaccharide. Other examples of BLOCKING GROUPS include carboxylic acid derivates, such as fatty acids and any other groups having a carboxyl moiety, and oligopeptide derivates.

Within the context of the BLOCKING GROUPS, the term "derivates" refers to the monovalent moiety generated by removal of a hydroxy group from the BLOCKING GROUP.

A "visible precipitate" means that the precipitate is detectable by visual inspection or by a light sensitive mechanism, e.g. a change in spectral (excitation/emission) properties.

The substrates of the present invention have considerably improved cell membrane permeability compared to other known fluorogenic enzyme substrates. This allows the fluorogenic substrates of the present invention to easily enter cells and therefore these substrates can be used for various applications in a wide variety of cells. For instance, the substrates described by U.S. Pat. No. 5,316,906 show very poor membrane permeability. In example 15 of that patent, intact fibroblast cells were treated with 100 μM of a galactosidase substrate. Once conditions were applied for allowing the formation of a fluorescent precipitate, maximum fluorescence intensity could only be observed after 6 hours. These data indicate very slow membrane permeation compared to classical permeable fluorescent compounds like calcein, rhodamine, thiazole orange, which reach steady state levels after approximately 30 minutes. In comparison, the substituted substrates of the present invention can start to produce fluorescent signals in living cells already after a few minutes or longer.

In addition to the improvement with respect to permeability characteristics, the precipitates of the present fluorogenic substrates have improved features when compared to other fluorescent agents such as for instance fluorescein-labelled secondary reagents. The fluorogenic substrates according to the present invention are generally soluble but non-fluorescent in water, however, they release a highly fluorescent precipitate in an aqueous solution containing the substrate and the corresponding enzyme. The substrates precipitate to form clear and bright fluorescent compounds upon action of the appropriate enzymes.

The substrates of the present invention show a rapid precipitation rate for the solid product released by action of the enzyme because they are efficiently recognized by the appropriate enzymes in enzymatic tests. Importantly the precipitates are formed upon enzymatic hydrolysis without compromising the enzymatic activity. The latter allows, for instance, their use for localization studies in biological specimens or detection of discrete bands in non-denaturing PAGE and in Western blotting.

Furthermore, the substrates of the present invention can be prepared with a variety of blocking groups, such as β-D-galactose and β-D-glucuronic acid derivates and are sufficiently specific to the corresponding β-D-galactosidase and β-D-glucuronidase enzymes, which recognize these derivates. Also a phosphate or sulfate blocking group is sufficiently specific to the corresponding phosphatase and sulfatase enzymes, which recognize these derivates. Interestingly, the staining produced with the substrate is sufficiently photostable allowing time to examine, focus and photograph the fluorescing matter under high magnification.

Another characteristic is that the precipitates of the fluorogenic substituted hydrolase substrates of the present invention, exhibit a Stokes shift frequently over 50 nm, often over 60, 80, 100, 120 nm, a feature that enhances the resolution of the signal fluorescence over the background, allowing the sensitive detection of a relatively small concentration of precipitated molecules in cells or tissues with little or no autofluorescence, as well as overcoming the problem of distinguishing signal to background in autofluorescent background. Also, the product's large Stokes shift makes the substrate ideal for multicolour applications.

In another embodiment, the present invention relates to a method for preparing a fluorogenic substrate according to the invention comprising the steps of:

synthesizing a blocking group, whereby said blocking group may be optionally protected;

synthesizing a substituted fluorophore;

coupling the optionally protected blocking group to said substituted fluorophore;

optionally deprotecting said blocking group; and purifying the resulting substituted substrate.

Derivates of mono- or polysaccharides are prepared by procedures known in the art (K. D. Larison et al., J. Histochem. Cytochem., 1995, 43, 77; J. C. Jaquinet, Carbohydr. Res., 1990, 199, 153; A. Nudelman et al., Carbohydr. Res., 1987, 162, 145).

Quinazolinones (quinazolones), benzimidazoles, benzothiazoles, benzoxazoles, quinolines, and indolines may be prepared by procedures common in the art that are extensively available in the literature (R. Pater, J. Heterocycl. Chem, 1971, 8, 699; J. J. Naleway et al., Tetrahedron Lett., 1994, 35, 8569; T. G Deligeorgiev, Dyes and Pigments, 1990, 12, 243).

For preparing substituted fluorophores, it is possible to introduce side chains directly onto the aromatic ring of a molecule by means of a Stille coupling followed by purification to remove impurities (J. K. Stille, Angew. Chem. Int. Ed. Eng., 1986, 25, 508). The chains can be introduced simultaneously on both aromatic rings. An alternative preferred method of preparation of di-substituted compounds comprises the synthesis of two monosubstituted parts first followed by a combination of the two parts to form the desired di-substituted compound (R. A. Coburn et al., J. Med. Chem., 1981, 1245; E. Vedejs, Org. Reactions, 1974, 401; G. Hahn, Deutsches Patentschrift, 869639, 1953; T. Tamura et at., European Patent Appl., 1.081.138A1, 2000). This method allows obtaining a higher yield while avoiding the presence of mono-substituted impurities in the final product.

The BLOCKING GROUP may be bound to the substituted fluorophores by reacting a reactive form of the BLOCKING GROUP with the hydroxyl, amino or mercapto groups present in the unbound form of the substituted fluorophoric group. This will result in the production of a non-fluorescent intermediate. The coupled BLOCKING GROUP moieties can show several protecting groups, which will be removed using a process appropriate to the protecting group(s) present. Particularly, if the BLOCKING GROUP moieties comprise glucuronic acid or galactose derivates, coupling can be achieved by means of a Schmidt coupling (R. R. Schmidt et al., Angew. Chem. Int. Ed. Eng., 1980, 19, 731). The BLOCKING GROUP can also be a sulfate or a phosphate group. A phosphate group can be coupled to the unbound form of the substituted fluorophoric group using diethylchlorophosphate as phosphorylating agent (Qing Zhu et al., Tetrahedron Lett., 2003, 44, 2671), followed by hydrolysis (A. K. Szardenings, Tetrahedron Lett., 1996, 37, 3638).

Finally, the formed substrates will be purified, especially when bis(tributyltin)methoxide in ether is used to perform the BLOCKING GROUP deprotecting step. In this case the purification step is needed to remove tin containing impurities which could cause the final product to be cytotoxic.

Using this preparation method, it is possible to obtain highly pure enzyme substrates, which hardly show any contamination with other compounds or impurities. Another important aspect is that this preparation method is specific, allowing the preparation of substrates in a rapid, efficient and cost-effective way.

In another embodiment, the present invention refers to a method for studying the activity of an enzyme comprising the steps of:

contacting a sample containing said enzyme with an enzyme substrate according to the invention;

applying conditions suitable to allow formation of a fluorescent precipitate according to the invention; and quantitatively or qualitatively analyzing said fluorescent precipitate.

"Sample" refers to any fluid, solid, jelly, emulsion, slurry, or a mixture thereof that contains a membrane compartment. A sample is preferably an aqueous solution that contains a cell, such as an eukaryotic cell such as a mammalian cell, or such as a human cell.

The substrate is combined with a sample under conditions suitable for the formation of the precipitate. The concentration of the substrate must be sufficient to give a detectable reaction product. Typically, the precipitate forms within several minutes after interaction of the substrate with the enzyme. Usually, optimal precipitation is obtained within about 5 minutes to about 2 hours, most preferably, within about 15 minutes to about 1 hour.

The present invention can be used to qualitatively or quantitatively detect the activity of any enzyme that is capable of cleaving the BLOCKING GROUP from the remainder of the molecule to yield a fluorescent detection product.

Analysis of the fluorescent precipitate may comprise the steps of (a) exposing the fluorescent precipitate to a light source capable of producing light at a wavelength of absorption of the fluorescent precipitate; and (b) detecting the resultant fluorescence of the precipitate. To facilitate the detection of the visible precipitate, the excitation or emission properties of the precipitate are utilized. For example, the fluorescent precipitate is excited by a light source capable of producing light at or near the wavelength of maximum absorption of the fluorescent product, such as an ultraviolet or visible lamp, an arc lamp, a laser, or even sunlight. Preferably the fluorescent precipitate is excited at a wavelength equal to or greater than about 250 nm, more preferably equal to or greater than about 300 nm, even more preferably equal to or greater than about 350, 370, 390, 400, 430, 450 nun. The fluorescence of the precipitate is detected by detection of the resultant light emission at a wavelength of greater than about 300 nm, to about 480, 500, 520, 540, 560, 580, 600 nm. The emission can be detected by means that include the use of instrumentation such as fluorometers, quantum counters, plate readers, microscopes and flow cytometers or by means for amplifying the signal such as a photomultiplier. Preferably, FACS systems or systems dedicated to high throughput screening, e.g 96 well or greater microtiter plates or multi-well platforms are used. Alternatively, analyzing the precipitate comprises detecting the precipitate by visual inspection or light scattering techniques.

A sample for studying activity of an enzyme may be a biological cell. A biological cell may be of animal, plant, bacterial or yeast origin. The cells may be living, or they may be dead. The cells may be isolated, in tissue, in vivo or in vitro. Preferably, the method of detecting enzyme activity of the present invention relates to the introduction of an enzyme substrate of the present invention in a plant cell or a mammalian cell. Many cells can be used for monitoring enzyme activity. Such cells include, but are not limited to, baby hamster kidney (BHK) cells, mouse L cells, Jurkats and 153 DG44 cells (see, Chasin (1986) Cell. Molec. Genet. 12: 555), human embryonic kidney (HEK) cells, Chinese hamster ovary (CHO) cells, PC12 cells, COS-7 cells and yeast, blood mononuclear cells (PBMCs), CD4+T-cell line, preferably the MT4 cell line or the HeLa CD4+ cell lines, and cancer cells. Cancer cells can be derived from any cancer of any internal or external organ system in the body.

Applications of the assay systems are versatile. The assay can be used to screen a cell or tissue for baseline activity of any enzyme of interest. The assay can be used with equal ease to screen for compounds that can either activate or inhibit the enzymes. That means the assay can be used to screen for drugs against degenerative diseases, drugs against cancer, antivirals, antibacterials, antifungals.

The assay can be used to screen for enzyme activation or inhibition in any living or dead cells or cell lines derived from any organ system in the body including, but not limited to, hair, brain, peripheral nervous system, eye, ear, nose, mouth, tonsils, teeth, esophagus, lung, heart, blood, blood vessels, bone marrow, lymph nodes, thymus, spleen, immune system, liver, stomach, intestinal tract, pancreas, endocrine glands and tissues, kidney, bladder, reproductive organs and glands, joints, bones and skin. The assay can be used to screen for drugs with potential use in any disease of any organ system in the body that involves malfunction of the appropriate enzyme.

The assay can be used to screen for drugs that might modulate the enzymes directly or indirectly, i.e. by modulating the enzymes itself or by modulating cellular receptors and co-factors that influence the enzymes or their cascades.

The assay can be used to determine the site of action at which an enzyme or its cascade modulator interferes. That is, the assay can help to pin down the molecular mechanism of action of a novel enzyme or its cascade modulator drugs.

The invention also relates to the use of subject fluorescent substrates for finding new compounds or new uses for known compounds in reducing, preventing or treating maladies in which (programmed) cell death, cell proliferation, or any abnormal cell behaviour is either a causative factor or a result. Examples of uses for the present invention include screening for compounds that can protect the nervous system following focal ischemia and global ischemia; screening for compounds that can treat neurodegenerative disorders such as Alzheimer's disease, Huntington's Disease, prion diseases, Parkinson's Disease, multiple sclerosis, amyotrophic lateral sclerosis, ataxia, telangiectasia, and spinobulbar atrophy; screening for compounds that can treat heart disease including myocardial infarction, congestive heart failure and cardiomyopathy; screening for compounds that can treat retinal disorders; screening for compounds that treat autoimmune disorders including lupus erythematosus, rheumatoid arthritis, type I diabetes, Sjogren's syndrome and glomerulonephritis; screening for compounds that treat polycystic kidney disease and anemia/erythropoiesis; screening for compounds that treat immune system disorders; screening for compounds that treat infectious diseases including AIDS, SCIDS, hepatitis and other gastrointestinal infections, tuberculosis and other respiratory infections, sexually transmitted infections other than HIV/AIDS; screening for compounds that reduce or prevent cell, tissue and organ damage during transplantation (e.g. graft versus host disease in bone marrow transplantation procedures); screening for compounds that reduce or prevent cell line death in industrial biotechnology; screening for compounds that reduce or prevent alopecia (hair loss); screening for compounds that reduce the premature death of skin cells.

Similarly, the present invention also relates to the use of the subject fluorescent substrates in screening procedures where libraries of known drugs or combinatorial or other compound libraries are screened for compounds with antiviral, anti-tumor or anti-cancer activity, for instance.

The present invention also relates to the use of the enzyme substrates in diagnostic procedures to determine the chemosensitivity or resistance of cancer cells taken from an animal or a human being to treatment with chemotherapeutic drugs. The cancer cells can be derived from any cancer of any internal or external organ system in the body. Further, the invention relates to methods for detecting an enzyme involved in the apoptosis cascade in one or more cells; measuring the activity of an enzyme involved in the apoptosis cascade in one or more cells; determining whether a test substance has an effect on an enzyme involved in the apoptosis cascade in one or more cells; determining the sensitivity of an animal with cancer to treatment with one or more chemotherapeutic agents; monitoring the treatment of an animal with one or more chemotherapeutic drugs; determining whether a test substance inhibits or prevents cell death in one or more test cells, whether a test substance causes or enhances cell death in one or more cells. Said methods may be accomplished by contacting the one or more cells with the enzyme substrate according to the invention under conditions whereby the substrate is taken into said one or more cells, and recording the fluorescence of said one or more cells, wherein a change in fluorescence, either of magnitude (i.e. increase) or of wave length, within the one or more cells compared to control cells which have not been so contacted or one that has been contacted with the substrate and a known competitive inhibitor of the enzyme, is an indication of the presence of the enzyme, or of the activity of the test substance, or of the chemosensitivity of the cancer cells to one or more agents.

Another application of the present invention, is the use of the enzyme substrates in detecting the cytopathogenic effect of replicating virus within cells, comprising (a) contacting the one or more viral infected cells with the enzyme substrates under conditions whereby the substrates are taken into the one or more viral infected cells, and (b) recording the fluorescence of said one or more cells, wherein a change in fluorescence within the one or more viral infected cells compared to control cells which have not been infected, is a measure of the activity of the viral enzymes and their cell-killing effect. In this indirect measuring method, the enzyme which converts the substrates of the present invention is not necessarily the viral enzyme, but a cellular enzyme. Similarly, the invention relates to methods for detecting any effect of replicating virus within cells in the presence of a test substance which has an effect on the virus; determining the sensitivity of an animal with HIV to treatment with one or more antiviral agents; monitoring the treatment of an animal with one or more antiviral drugs; determining whether a test substance inhibits or prevents viral replication in one or more test cells.

In studying enzyme activity, the enzyme upon evaluation may be present in the cell either as the result of expression of an endogenous gene or of a foreign gene introduced by means of viral transfection or genetic manipulation. More particularly, enzyme activity analyses may be translated to gene expression analyses or promoter studies. The enzyme being evaluated may be encoded by a reporter gene. Reporter genes encode for enzymes capable of catalyzing the conversion of specific substrates into their corresponding fluorescent precipitates. In general, reporter genes are nucleic acid sequences encoding easily assayed proteins. Alternatively, they can be used to replace other coding regions whose protein products are difficult to test. Examples of reporter genes include the *Escherichia coli* lacZ gene, which encodes β-D-galactosidase (GAL) enzyme, in animals and yeasts, the *Escherichia coli* gusA (uidA) reporter gene, which encodes β-D-glucuronidase (GUS) in plants.

Reporter genes can "report" many different properties and events including enzymatic expression levels; gene expression; specificity and strength of promoters, whether native or modified for reverse genetic studies; the efficiency of gene delivery systems; the intracellular fate of a gene product which can be a result of protein traffic; interaction of two proteins in the two-hybrid system or of a protein and a nucleic acid in the one-hybrid system; the efficiency of translation initiation signals; a metabolic status; a disease state; the identity or presence of micro-organisms; the quantity of toxins; and the success of genetic manipulation and molecular cloning efforts.

Reporter genes are often fused with genomic regulatory elements, for instance, promoters. The resulting DNA constructs are then introduced into the cell of interest, and the enzyme expression is assayed to ensure proper gene expression. Using this technique, one can investigate expression efficiency of the encoding gene, which may be affected by promoter and/or repressor manipulations. This kind of technique may also be used to evaluate the expression pattern of a promoter of interest.

The substrates can also be used to probe cell populations or inert samples for cells expressing the enzyme of interest. For example, because the GUS and GAL enzymes are both issued from *E. coli*, their presence in some sample may indicate bacterial contamination of the biological samples.

The fluorescent substrates can also be designed to measure more than one enzyme at a time, for instance in "multiplex" type assays, by designing substrates that are recognized and cleaved for instance by more than one of the enzymes involved in a same metabolic path. Fluorogenic substrates which are "promiscuous" for more than one enzyme may be utilized using the assay process described herein to measure the activity of as yet unknown enzymes. As well, different fluorescent substrates which absorb at the same wavelength and emit at different wavelengths may be employed in an assay to measure simultaneously the activity of different enzymes.

In the practice, the test cells may be contacted with a test substance prior to, after, or substantially simultaneously with the fluorogenic substrates according to the invention. The method may be used to detect whether the test substance stimulates or inhibits the activity of the enzyme. The invention also relates to further contacting the test cells with a second test substance or mixture of test substances in the presence of the first test substance.

Suitable solubilizers may be used for presenting the fluorogenic substrates of the present invention to tissues, cells or cell lines. Suitable solubilizers include aqueous solutions of the substrates in water-soluble form, for example, water-soluble salts and buffered solutions. In addition, emulsions and suspensions of the compounds as appropriate oily suspensions may be presented to the cells or tissues. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400) or dimethylsulfoxide (DMSO) or another suitable solubilizer. Optionally, the emulsion, suspension or solution may also contain stabilizers. Optionally, electroporation or presentation of the reporter molecules in liposomes or detergents may be used to enhance the cell permeability of the fluorogenic reporter molecules.

Multi-well platforms useful in the present invention can have between about 6 and about 5,000 wells, preferably between about 96 and about 4,000 wells, most preferably in multiples of 96.

Preparations of preferred substrates are described herein as a means of illustrating the reactions. The descriptions are meant to illustrate, and not to limit the choice of reactants and reaction conditions that can be used to prepare the requisite fluorogenic substrates. By appropriate choice of substituents, in particular, the properties of membrane permeability, solubility, fluorescence intensity and wavelengths and product photostability can be modified.

EXAMPLES

Example 1

Quick Test for Enzyme Recognition of GUS Substrates

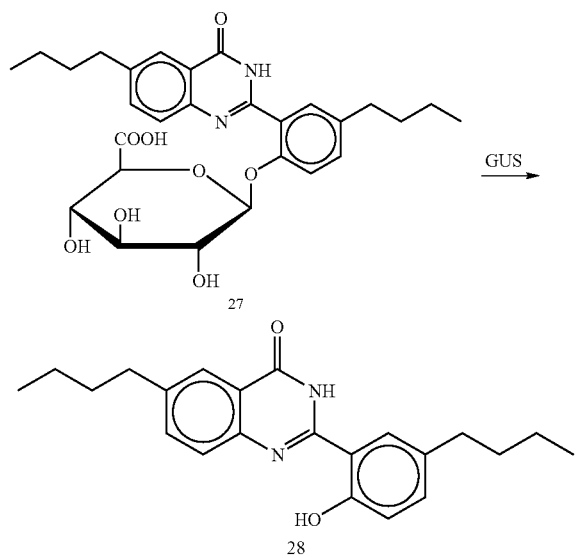

Dibutyl GUS substrate (compound 27) was tested. First a solution of 2 mg of product (compound 27) in 2 ml pH 8 buffer solution (Merck Titrisol 9888) was made. 1 ml of this solution was kept aside, to the other 1 ml solution 5 µl (500 UNITS) β-D-glucuronidase from *Helix Pommatia* type HP-2 (Sigma G7017) was added. After 15 minutes of shaking at room temperature both solutions were spotted on a TLC-plate (Macherey-Nagel SIL G-25 UV$_{254}$). The plate was developed using isooctane/acetone 60:40. The solution containing GUS enzyme showed a clear fluorescent spot on the TLC plate (Rf=0.53), the blank solution showed no fluorescent spot. This showed that the GUS enzyme used could convert non-fluorescent substrate (compound 27) into fluorescent product (compound 28).

Example 2

Preparation of an Activated Protected Sugar Moiety (Protected BLOCKING GROUP)

D-glucurono-6, 3-lactone

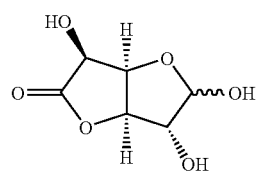

60% | 1) MeOH/NaOH
    | 2) Ac$_2$O/pyridine

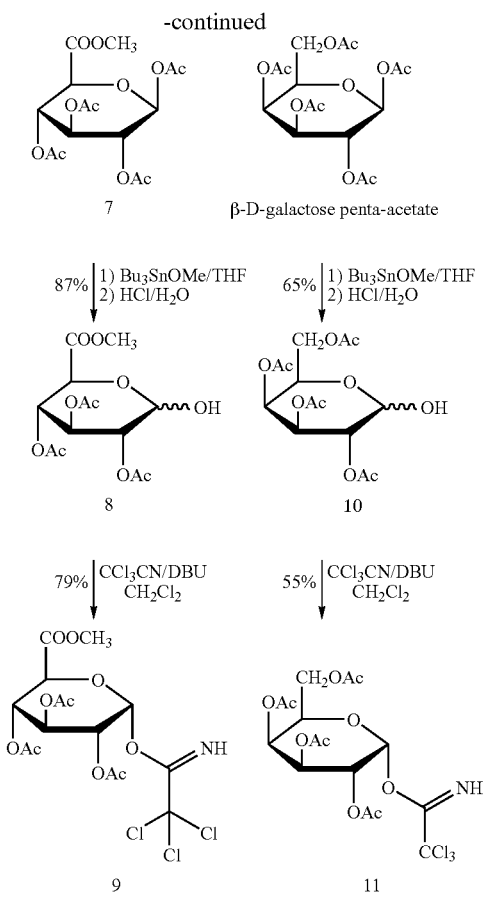

β-D-galactose penta-acetate

Methyl (1,2,3,4-tetra-O-acetyl-β-D-glucuronate) (compound 7). D-glucurono-6,3-lactone (19.0 g, 108 mmole) was suspended in 250 ml MeOH and stirred at r.t. under argon. A solution of 100 mg NaOH in 100 ml MeOH was slowly added (1 h). After stirring for an additional hour, the mixture was concentrated under reduced pressure and placed in an ice bath. Pyridine (45 ml, 562 mmole) and acetic anhydride (54 ml, 652 mmole) were added keeping the temperature below 10° C. After the residue was dissolved, the mixture was stirred for 3 hours at r.t. and then concentrated under reduced pressure until almost solid. Dichloromethane (300 ml) was added, the residue was dissolved and washed 3 times with 100 ml water and dried on MgSO$_4$. After MgSO$_4$ was removed, 200 ml MeOH was added, the precipitate filtered off and dried. White crystals were obtained (25.0 g, 65% yield). The product consisted of 100% β form.

$^1$H-NMR: (500 MHz, CDCl$_3$): δ (ppm): 5.75 (d, 8.0 Hz, 1H), 5.31 (dd ap. t, 9.3 Hz, 1H), 5.24 (dd ap. t, 9.3 Hz, 1H), 5.14 (dd, 9.3/8.0 Hz, 1H), 4.18 (d, 9.3 Hz, 1H), 3.34 (s, 3H), 2.12 (s, 3H), 2.03 (m, 9H).

$^{13}$C-NMR: (50 MHz, CDCl$_3$): ν (ppm): 169.9, 169.4, 169.2, 168.8, 166.9, 91.4, 73.0, 71.8, 70.2, 69.0, 53.0, 20.8, 20.6, 20.5.

IR (film): ν (cm$^{-1}$): 2959 (w), 1757 (s), 1447 (w), 1370 (m), 1217 (s), 1091 (m), 1041 (m), 978 (w), 911 (w), 895 (w), 772 (w), 692 (w), 600 (w), 558 (w).

Methyl (2,3,4-tri-O-acetyl-α/β-D-glucuronate) (compound 8). To a solution of compound 7 (36.1 g, 96 mmole) in 600 ml dry THF, 28.8 ml tributyltinmethoxide (100 mmole) was added. The flask was flushed with argon and the mixture was heated until reflux for 5 hours. The solvent was removed under reduced pressure. 200 ml 0.5 M HCl was added and the mixture was extracted 2 times with 300 ml dichloromethane. The combined organic layers were dried on MgSO$_4$, and the solvent evaporated under reduced pressure. The residue was kept at −20° C. overnight. Two layers were formed. The top layer was removed. The bottom layer was purified by flash chromatography (Acros Silicagel 0.060-0.200 mm) using isooctane/ethyl acetate 50:50. A white solid (26.0 g, 80% yield) was obtained, consisting of 78% α and 22% β product.

$^1$H-NMR: (500 MHz, CDCl$_3$+dr D$_2$O): δ (ppm): 5.58 (dd ap. t, 9.8 Hz, 1H$_\alpha$), 5.55 (d, 3.6 Hz, 1H$_\alpha$), 5.31 (dd ap. t, 9.6 Hz, 1H$_\beta$), 5.23 (dd ap. t, 9.6 Hz, 1H$_\beta$), 5.18 (dd ap. t, 9.8 Hz, 1H$_\alpha$), 4.91 (m, 1H$_\alpha$+1H$_\beta$), 4.79 (d, 7.7 Hz, 1H$_\beta$), 4.59 (d, 9.8 Hz, 1H$_\alpha$), 4.10 (d, 9.6 Hz, 1H$_\beta$), 3.76 (s, 3H$_\beta$), 3.75 (s, 3H$_\alpha$), 2.09 (s, 3H$_\beta$), 2.08 (s, 3H$_\alpha$), 2.03 (m, 6H$_\alpha$6H$_\beta$).

$^{13}$C-NMR: (50 MHz, CDCl$_3$): δ (ppm): 170.4, 170.2, 169.9, 169.8, 168.7, 167.8, 95.3, 90.2, 72.7, 72.4, 71.8, 70.9, 69.6, 69.5, 69.2, 67.9, 53.0, 52.9, 20.7, 20.5.

IR (film): ν (cm$^{-1}$): 3441 (s, broad), 2958 (w), 1754 (s), 1437 (m), 1374 (m), 1228 (s), 1157 (m), 1071 (s), 936 (w), 898 (w), 841 (w), 798 (w).

Methyl (1-deoxy-2,3,4-tri-O-acetyl-1-trichloroacetimidoyl-α-D-glucuronate) (compound 9). 13.1 g compound 8 (39.2 mmole) was dissolved in 80 ml dry dichloromethane. 20.0 ml Trichloroacetonitrile (195.9 mmole) and 0.6 ml DBU (3.9 mmole) were added. The mixture was stirred for 24 h at r.t. under argon. To the solution was added 3 g of fine silica, the mixture was stirred for 5 min. and filtered. The filtrate was concentrated under reduced pressure and purified with flash chromatography (Acros Silicagel 0.060-0.200 mm) using pentane/ethyl acetate 75:25. A white solid was obtained (15.0 g, 79% yield), consisting of 100% α form.

$^1$H-NMR: (500 MHz, CDCl$_3$): δ (ppm): 8.73 (s, 1H), 6.64 (d, 3.6 Hz, 1H), 5.63 (dd ap. t, 10.1 Hz, 1H), 5.27 (dd ap. t, 10.1 Hz, 1H), 5.15 (dd, 10.1/3.6 Hz, 1H), 4.50 (d, 10.1 Hz, 1H), 3.75 (s, 3H), 2.05 (m, 6H), 2.01 (s, 3H).

$^{13}$C-NMR: (50 MHz, CDCl$_3$): δ (ppm): 169.8, 169.7, 169.5, 167.2, 160.5, 92.6, 90.5, 70.5, 69.4, 69.1, 68.9, 53.1, 20.7, 20.5, 20.4.

IR (film): ν (cm$^{-1}$): 3320 (w), 2957 (w), 1756 (s), 1679 (m), 1439 (w), 1370 (m), 1287 (w), 1218 (s), 1150 (w), 1043 (s), 971 (m), 914 (w), 835 (w), 797 (m), 734 (w), 697 (w), 645 (w), 600 (w), 552 (w).

2,3,4,5-Tetra-O-acetyl-α/β-D-galactose (compound 10). To a solution of commercially available β-D-galactose penta-acetate (12.0 g, 31 mmole) in 500 ml dry THF, 9.3 ml tributyltinmethoxide (32 mmole) was added. The flask was flushed with argon and the mixture was heated until reflux for 5 hours. The solvent was removed under reduced pressure. 200 ml 0.5 M HCl was added and the mixture was extracted twice with 300 ml dichloromethane. The combined organic layers were dried on MgSO$_4$, and the solvent evaporated under reduced pressure. 150 ml Acetonitrile was added and this layer was washed 6 times with 150 ml n-hexane to remove tin residues. The solvent was evaporated and the residue was purified with flash chromatography (Acros Silicagel 0.060-0.200 mm) using isooctane/ethyl acetate 70:30. A white solid (7.0 g, 65% yield) was obtained, consisting of 70% α and 30% β product.

$^1$H-NMR: (500 MHz, CDCl$_3$): δ (ppm): 5.52 (d, 3.5 Hz, 1H$_\alpha$), 5.48 (m ap. d, 1H$_\alpha$), 5.41 (m, 1H$_\alpha$+1H$_\beta$), 5.17 (dd, 3.5/10.8 Hz, 1H$_\alpha$), 5.07 (m, 2H$_\beta$), 4.69 (m, 1H$_\beta$), 4.47 (t, 6.5 Hz, 1H$_\alpha$), 4.10 (m, 2H$_\alpha$+2H$_\beta$), 3.96 (t, 6.5 Hz, 1H$_\beta$), 2.16 (s, 3H$_\beta$), 2.15 (s, 6H$_\alpha$), 2.11 (s, 3H$_\beta$), 2.10 (s, 3H$_\alpha$), 2.05 (m, 3H$_\alpha$+3H$_\beta$), 2.00 (s, 3H$_\beta$), 1.99 (s, 3H$_\alpha$).

IR (film): ν (cm$^{-1}$): 3464 (m, broad), 2971 (w), 1747 (s), 1434 (w), 1372 (m), 1231 (s), 1154 (w), 1126 (w), 1052 (s), 956 (w), 913 (w), 774 (w), 736 (w), 703 (w), 601 (w).

1-Deoxy-2,3,4,5-tetra-O-acetyl-1-trichloroacetimidoyl-α-D-galactose (compound 11). 6.4 g compound 10 (20.0 mmole) was dissolved in 60 ml dry dichloromethane. 10.0 ml Trichloroacetonitrile (100.0 mmole) and 0.3 ml DBU (2.0 mmole) were added. The mixture was stirred for 24 h at r.t. under argon. Solvents were evaporated and the resulting residue was purified by flash chromatography (Acros Silicagel 0.060-0.200 mm) using isooctane/acetone 85:15. A white solid was obtained (5.4 g, 55% yield), consisting of 100% α form compound 11.

$^1$H-NMR: (500 MHz, CDCl$_3$): δ (ppm): 8.67 (s, 1H), 6.60 (d, 3.5 Hz, 1H), 5.56 (m, 1H), 5.42 (dd, 3.3/10.8 Hz, 1H), 5.36 (dd, 3.4/10.8 Hz, 1H), 4.44 (t, 7.0 Hz, 1H), 4.13 (m, 2H), 2.17 (s, 3H), 2.02 (m, 9H).

IR (film): ν (cm$^{-1}$): 1751 (s), 1677 (w), 1431 (w), 1371 (m), 1225 (s), 1149 (w), 1073 (m), 971 (w), 951 (w), 933 (w), 903 (w), 836 (w), 797 (w), 642 (w), 526 (w), 471 (w).

Example 3

Use of a Stille Coupling in Preparation of Dibutylated Quinazolinone Fluorophore (Compound 13)

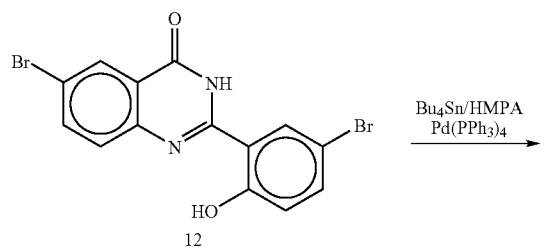

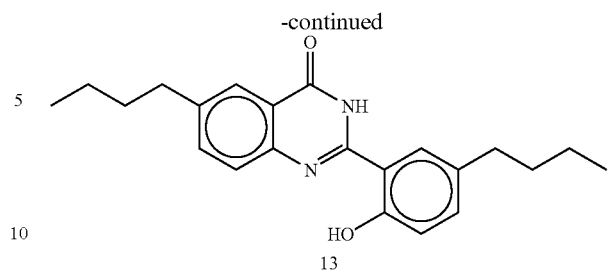

1.00 g Dibromide compound 12 (2.5 mmole) was dissolved in 10 ml HMPA, and subsequently 4.20 ml tetrabutyl tin (12.8 mmole) and 80 mg Pd(PPh$_3$)$_4$ (0.07 mmole) were added. The reaction mixture was heated at 80° C. for 5 days, followed by filtration. The filtrate was directly purified by flash chromatography using cyclohexane-acetone 95:5 as eluent. The fractions containing the desired product were collected, evaporated and purified again using cyclohexane-ethyl acetate 90:10. The obtained residue was washed once with 3 ml MeOH and dried, affording 155 mg (14% yield) of compound 13 as pale green crystals.

ES-MS (+) mode: 351.2 (M+H$^+$), 373.2 (M+Na$^+$)

$^1$H-NMR: (500 MHz, CDCl$_3$): δ (ppm): 8.14 (s, 1H), 8.02 (d ap. m, 1H), 7.64 (m, 2H), 7.29 (dd, 2.0/8.4 Hz, 1H), 7.02 (d, 8.4 Hz, 1H), 2.76 (m, 4H), 1.70 (m, 4H), 1.40 (r, 4H), 0.95 (m, 6H)

IR (film): ν (cm$^{-1}$): 2926 (w), 2834 (w), 1666 (s), 1616 (w), 1576 (w), 1505 (w), 1392 (w), 1339 (w), 973 (w), 810 (w).

Example 4

Preparation of Di-Pentylated Quinazolinone Fluorophore (Compound 21)

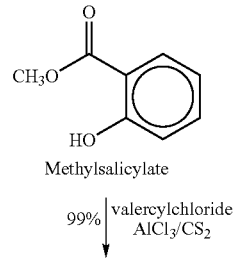

Methylsalicylate

99% | valercylchloride
AlCl$_3$/CS$_2$

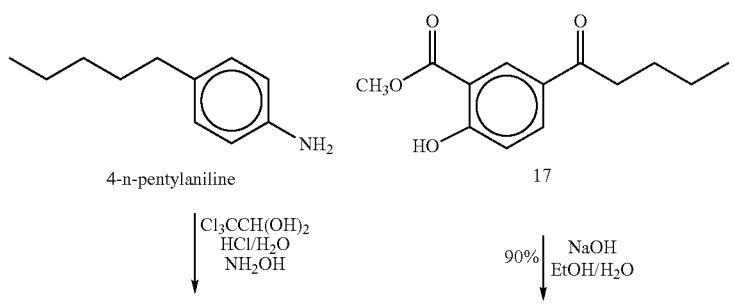

4-n-pentylaniline

Cl$_3$CCH(OH)$_2$
HCl/H$_2$O
NH$_2$OH

90% | NaOH
EtOH/H$_2$O

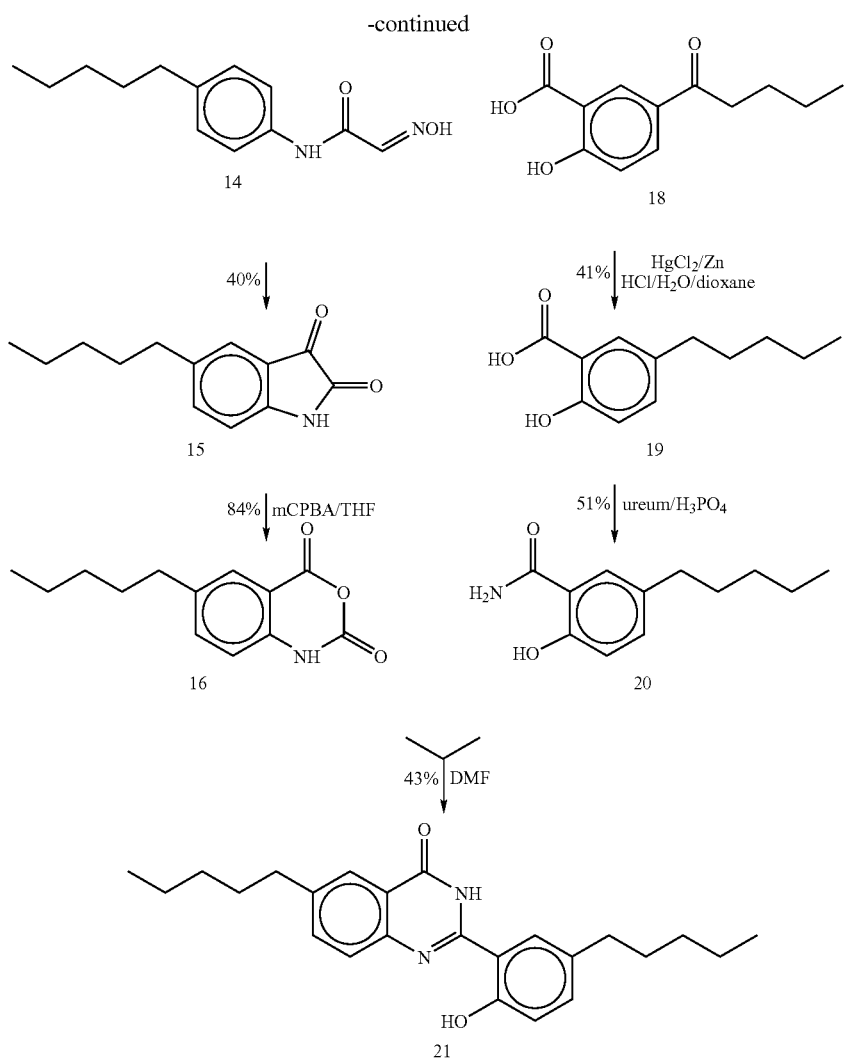

An alternative to dialkylation via a Stille coupling was to synthesize separately both monoalkylated building blocks, and then combine them to a lipophilic dialkylated fluorochrome. As an example, the synthesis of dipentylated fluorochrome (compound 21) is shown:

Synthesis of 5-n-pentylisatine (compound 15). 28.5 g Chloral hydrate (172 mmole) and 170 g sodium sulphate were dissolved in 600 ml water (solution 1). 27.8 ml 4-n-Pentylaniline (157 mmole) was dissolved with 15 ml concentrated HCl in 475 ml water (solution 2). 29.6 ml 50% Aqueous hydroxylamine was dissolved with 42 ml concentrated HCl in 80 ml water (solution 3). While stirring, solution 1 was heated to 60° C., then solution 2 followed by solution 3 were added dropwise. The temperature was raised until reflux for 15 minutes. The reaction mixture was allowed to cool down to room temperature. The solid residue was filtered off, dissolved in 500 ml ethyl acetate and washed three times with 200 ml water. After evaporation, the residue, mainly containing compound 14, was slowly added to an ice cooled beaker containing 100 ml concentrated sulphuric acid, while stirring. After all compound 14 was added, the reaction mixture was allowed to reach room temperature followed by heating at 80° C. for 15 minutes. 1000 g Ice was added and the formed solid was filtered and redissolved in 300 ml ethyl acetate. This solution was washed three times with 200 ml water and evaporated. The resulting residue was purified by flash chromatography (Acros Silicagel 0.060-0.200 mm) using isooctane/acetone 65:35, affording compound 15 as an orange solid (11.4 g, 40% yield).

$^1$H-NMR: (500 MHz, CDCl$_3$): δ (ppm): 9.35 (s, 1H), 7.38 (d ap. s, 1H), 7.35 (dd, 1.7/8.0 Hz, 1H), 6.92 (d, 8.0 Hz, 1H), 2.54 (t, 7.6 Hz, 2H), 1.57 (m, 2H), 1.30 (m, 4H), 0.88 (t, 6.9 Hz, 3H).

IR (film): ν (cm$^{-1}$): 3279 (w), 2955 (w), 2856 (w), 1745 (s), 1624 (s), 1490 (s), 1197 (w), 657 (w).

Synthesis of 5-n-pentylisatoic anhydride (compound 16). 8.13 g of compound 15 (37.5 mmole) was dissolved in 145 ml THF. This solution was added dropwise to a solution of 12.9 g m-chloro-perbenzoic acid (74.8 mmole) in 55 ml THF and stirred overnight. To the reaction mixture 150 ml saturated sodiumbicarbonate and 500 ml water were added. The resulting suspension was extracted three times with 250 ml ethyl acetate. After evaporation compound 16 was obtained as a white solid (7.4 g, 84% yield).

$^1$H-NMR: (500 MHz, CDCl$_3$): δ (ppm): 9.95 (s, 1H), 7.87 (d ap. s, 1H), 7.51 (dd, 1.6/8.2 Hz, 1H), 7.08 (d, 8.2 Hz, 1H), 2.63 (t, 7.6 Hz, 2H), 1.61 (m, 2H), 1.30 (m, 4H), 0.88 (t, 6.9 Hz, 3H).

IR (film): ν (cm$^{-1}$): 3246 (w), 2955 (w), 2927 (w), 2856 (w), 1789 (m), 1758 (s), 1697 (m), 1518 (w), 1350 (w), 1278 (w), 1140 (w), 1043 (w), 1004 (w), 847 (w), 765 (w), 750 (w), 679 (w), 580 (w), 556 (w).

Synthesis of methyl-5-n-pentanoyl salicylate (compound 17). 167 g Aluminum trichloride (1250 mmole) was put in 430 ml carbon disulfide and cooled to 5° C. A solution of 54 ml (418 mmole) methyl salicylate and 101 ml valeroyl chloride (835 mmole) in 145 ml carbon disulfide was added dropwise under mechanical stirring, and stirring was continued at room temperature for 20 h. Afterwards, the mixture was poured onto 2 kg ice, containing 100 ml concentrated HCl. After melting of the ice, 50 g sodium chloride was added and the mixture was extracted twice with 500 ml dichloromethane. The collected organic layers were washed three times with 300 ml brine, yielding after evaporation a clear liquid (98 g, 99% yield). No further purification was performed.

$^1$H-NMR: (500 MHz, CDCl$_3$): δ (ppm): 8.49 (d, 2.3 Hz, 1H), 8.09 (dd, 2.3/8.8 Hz, 1H), 7.03 (d, 8.8 Hz, 1H), 4.0 (s, 3H), 2.92 (t, 7.4 Hz, 2H), 1.72 (m, 2H), 1.41 (m, 2H), 0.96 (t, 7.3 Hz, 3H).

IR (film): ν (cm$^{-1}$): 2958 (m), 2872 (w), 1674 (s), 1590 (m), 1444 (m), 1298 (w), 1266 (w), 1214 (s), 1088 (m), 961 (w), 843 (w), 796 (w), 731 (w), 688 (w), 584 (w).

Synthesis of 5-n-pentanoyl salicylic acid (compound 18). 97.5 g of compound 17 (412 mmole) was dissolved in 530 ml EtOH and 1050 ml water. 87 g NaOH (2.19 mole) was added and the mixture was refluxed for 5 hours. Afterwards the mixture was acidified with concentrated HCl to pH 1. The formed precipitate was filtered off and dried under reduced pressure. 82 g was obtained (90% yield).

$^1$H-NMR: (500 MHz, DMSO-d$_6$): δ (ppm): 8.38 (d, 2.3 Hz, 1H), 8.10 (dd, 2.3/8.7 Hz, 1H), 7.06 (d, 8.7 Hz, 1H), 2.95 (t, 7.3 Hz, 2H), 1.58 (m, 2H), 1.34 (m, 2H), 0.90 (t, 7.3 Hz, 3H).

ES-MS (+) mode: 223.0 (M+H$^+$), 245.0 (M+Na$^+$)

IR (film): ν (cm$^{-1}$): 3500 (w), 3072 (m, broad), 2955 (w), 2933 (w), 2869 (w), 1668 (s), 1588 (w), 1490 (w), 1428 (w), 1348 (w), 1301 (w), 1272 (w), 1198 (s), 1087 (w), 843 (w), 796 (w), 765 (w), 619 (w).

Synthesis of 5-n-pentyl salicylic acid (compound 19). 113 g Mossy zinc and 12.2 g HgCl$_2$ were shaken overnight in 4.6 ml concentrated HCl and 190 ml water. The clear liquid was decanted and 105 ml water, 56 ml concentrated HCl and 50 g compound 18 were added. The mixture was refluxed for 5 days. After cooling down the mixture it was extracted with 1000 ml EtOAc. The obtained organic layer was washed twice with brine, dried over magnesium sulphate and evaporated. The resulting residue was purified by flash chromatography (Acros Silicagel 0.060-0.200 mm) using dichloromethane/acetic acid 99:1, affording compound 19 as a white powder (19.6 g, 40% yield).

$^1$H-NMR: (500M, CDCl$_3$): δ (ppm): 9.90 (s, 1H), 7.88 (d, 1.6 Hz, 1H), 7.51 (dd, 1.6/8.3 Hz, 1H), 7.07 (di, 8.3 Hz, 1H), 2.64 (t, 7.6 Hz, 2H), 1.61 (m, 2H), 1.32 (m, 4H), 0.88 (t, 6.9 Hz, 3H).

ES-MS (−) mode: 207.1 (M−H$^+$).

IR (film): ν (cm$^{-1}$): 3248 (w, broad), 2924 (w), 1667 (s), 1614 (w), 1584 (w), 1487 (w), 1446 (s), 1334 (w), 1294 (w), 1216 (m), 902 (w), 794 (w), 675 (m), 581 (w), 471 (w).

Synthesis of 5-n-pentyl salicylamide (compound 20). 18 g compound 19 (86 mmole), 20.8 g ureum (346 mmole) and 5 drops polyphosphoric acid were heated at 150° C. during 18 h. After cooling, 500 ml EtOAc was added and the resulting solution was washed twice with brine. After evaporation of the organic phase, the resulting residue was purified by flash chromatography (Acros Silicagel 0.060-0.200 mm) using cyclohexane/isopropanol 95:5, affording compound 20 as a white powder (9.17 g, 51% yield).

$^1$H-NMR: (500M, CDCl$_3$): δ (ppm): 7.25 (dd, 2.0/8.5 Hz, 1H), 7.15 (d, 2.0 Hz, 1H), 6.92 (d, 8.5 Hz, 1H), 2.53 (t, 7.6 Hz, 2H), 1.56 (m, 2H), 1.30 (m, 4H), 0.88 (t, 6.9 Hz, 3H).

IR (film): ν (cm$^{-1}$): 3408 (s, broad), 3196 (w), 2953 (w), 2854 (w), 1660 (s), 1634 (s), 1497 (m), 1436 (w), 1356 (w), 1249 (m), 1138 (w), 1081 (w), 822 (w), 795 (w), 744 (w), 695 (w), 580 (w).

Synthesis of 2-(2-hydroxy-5-n-pentylphenyl)-6-n-pentyl-3H-quinazolin-4-one (compound 21). 2.81 g compound 16 (12.1 mmole) and 2.50 g (112.1 mmole) compound 20 were heated at 150° C. in 10 ml DMF for 3.5 h. The mixture was slowly cooled down to room temperature, the formed crystals were isolated by filtration and washed with 3 ml MeOH. After drying, 2 g of compound 21 was obtained as pale green crystals (43% yield).

$^1$H-NMR: (500 MHz DMSO-d$_6$): δ (ppm): 8.08 (s, 1H), 7.95 (s, 1H), 7.69 (dd, 1.6/8.3 Hz, 1H), 7.66 (d, 8.3 Hz, 1H), 7.26 (dd, 1.6/8.3 Hz, 1H), 6.90 (d, 8.3 Hz, 1H), 2.74 (t, 7.5 Hz, 2H), 2.55 (t, 7.5 Hz, 2H), 1.63 (m, 4H), 1.32 (m, 8H), 0.89 (m, 6H).

IR (film): ν (cm$^{-1}$): 2924 (w), 1666 (s), 1615 (w), 1592 (w), 1578 (w), 1505 (m), 1396 (w), 1336 (w), 1254 (w), 1226 (w), 1204 (w), 1150 (w), 1131 (w), 886 (w), 825 (w). Melting point: 244° C.

Example 5

Coupling of Activated Protected Glucuronic Acid (Compound 9) to Di-Pentylated Quinazolinone Fluorochrome (Compound 21) Followed by Deprotection of the Sugar Moiety

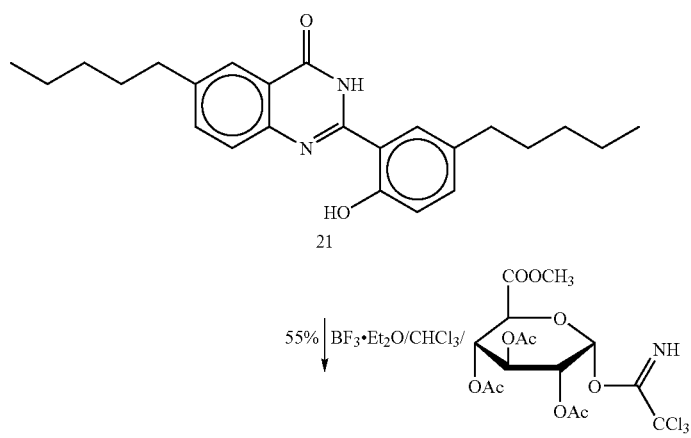

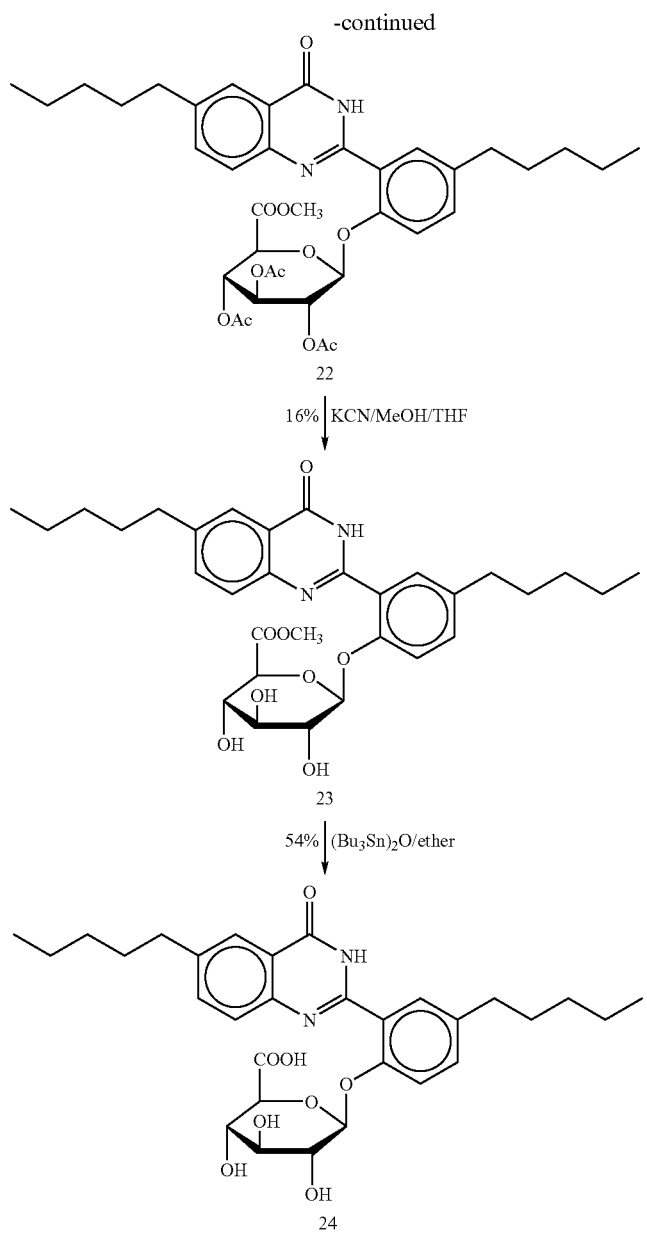

Synthesis of methyl 2,3,4-tri-O-acetyl-1-O-(2-(4-oxo-6-n-pentyl-3H-quinazolinyl)-4-n-pentylphenyl) β-D-glucuronate (compound 22). 0.378 g compound 21 (0.99 mmole) and 0.574 g of compound 9 (1.20 mmole) were excessively dried under reduced pressure and then dissolved in 11 ml dry chloroform. 13 μl Boron trifluoroetherate (0.099 mmole) was added and the reaction was stirred for 2 days at 30° C. The reaction mixture was evaporated and the resulting residue was purified by flash chromatography (Acros Silicagel 0.060-0.200 mm) using cyclohexane/acetone 90:10, affording compound 22 as a pale green powder (457 mg, 66% yield).

$^1$H-NMR: (500 MHz, DMSO-$d_6$): δ (ppm): 8.32 (d, 2.2 Hz, 1H), 8.00 (d, 8.6 Hz, 1H), 7.91 (dd, 1.9/8.6 Hz, 1H), 7.80 (d, 1.4 Hz, 1H), 7.26 (dd, 2.2/8.3 Hz, 1H), 6.91 (d, 8.3 Hz, 1H), 6.88 (d, 7.9 Hz, 1H), 5.84 (dd ap. t, 9.34 Hz, 1H), 5.41 (dd, 7.9/9.4 Hz, 1H), 5.19 (dd ap. t, 9.4 Hz, 1H), 4.98 (d, 9.4 Hz, 1H), 3.57 (s, 3H), 2.80 (m, 2H), 2.63 (m, 2H), 2.06 (s, 3H), 2.05 (s, 3H), 1.96 (s, 3H), 1.67 (m, 4H), 1.32 (m, 8H), 0.88 (m, 6H).

IR (film): ν (cm$^{-1}$): 3371 (w), 2925 (w), 2855 (w), 1749 (s), 1694 (s), 1614 (w), 1580 (w), 1504 (w), 1454 (w), 1428 (w), 1355 (w), 1232 (s), 1098 (m), 1061 (w), 834 (m), 753 (w), 650 (w), 605 (w).

ES-MS (+) mode: 695.3 (M+H$^+$).

Synthesis of methyl 1-O-(2-(4-oxo-6-n-pentyl-3H-quinazolinyl)-4-n-pentylphenyl) β-D-glucuronate (compound 23). 457 mg of compound 22 (0.66 mmole) was dissolved in 66 ml dichloromethane. 86 ml Potassium cyanide in methanol (0.25 g/ml) was added. The mixture was stirred for 40 h at room temperature. The reaction mixture was evaporated and the resulting residue was purified by flash chromatography (Acros Silicagel 0.060-0.200 mm) using cyclohexane/acetone 77:23, affording compound 23 as a pale green sticky solid (61 mg, 16% yield).

$^1$H-NMR: (500 MHz, DMSO-$d_6$): δ (ppm): 8.25 (d, 2.2 Hz, 1H), 8.05 (d, 1.2 Hz, 1H), 7.97 (d, 8.6 Hz, 1H), 7.91 (dd, 1.9/8.6 Hz, 1H), 7.27 (dd, 2.2/8.3 Hz, 1H), 6.91 (d, 8.3 Hz, 1H), 6.24 (d, 8.0 Hz, 1H), 5.70 (d, 5.3 Hz, 1H), 5.59 (d, 5.4

Hz, 1H), 5.45 (d, 4.9 Hz, 1H), 4.19 (d, 9.3 Hz, 1H), 3.64 (s, 3H), 3.55 (m, 2H), 2.82 (m, 2H), 2.63 (m, 2H), 1.65 (m, 4H), 1.33 (m, 8H), 0.88 (m, 6H).

Synthesis of 1-O-(2-(4-oxo-6-n-pentyl-3H-quinazolinyl)-4-n-pentylphenyl)-β-D-glucuronic acid (compound 24). 15 mg of compound 23 (0.027 mmole) was dissolved in 6 ml dry THF. 35 µl Bis-(tributyltin) oxide (0.069 mmole) was added and the reaction was stirred for 20 days at room temperature. 5 ml Acetonitrile was added and the mixture was washed 10 times with 5 ml n-hexane. The solvent was evaporated and the resulting residue was purified using a Phenomenex Luna C18(2) 22×250 mm 5µ HPLC column. A 10 minute gradient was used from 100% water (5 mM ammonium acetate) to 100% acetonitrile. The UV detector wavelength was set at 270 nm. The first eluting peak was isolated and lyophilized. 8 mg of a white solid was obtained (54% yield). An electrospray mass spectrum showed the correct mass.

ES-MS (−) mode: 553.2 (M−H$^+$), 1107.6 (2M−H$^+$).

GUS substrate (compound 24) was tested and it showed a clear positive reaction after 30 minutes.

Example 6

Coupling of a Phosphate Group to Di-Butylated Quinazolinone Fluorophore (Compound 21)

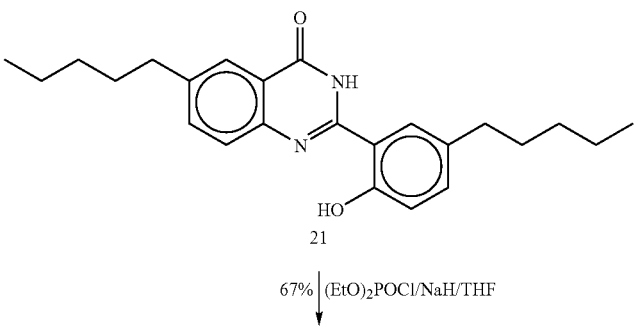

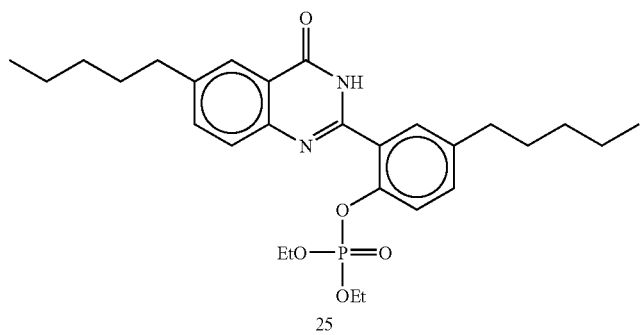

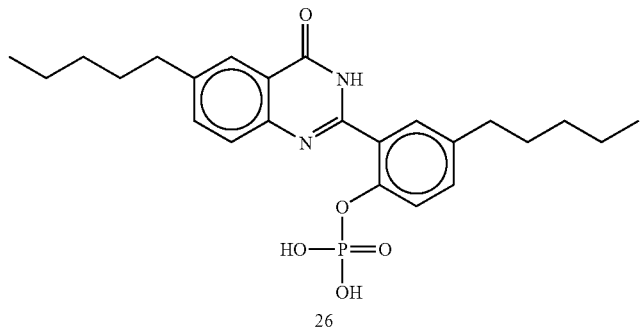

Synthesis of 2-(2-diethylphosphoryloxy-5-n-pentylphenyl)-6-n-pentyl-3-H-quinazolin-4-on (compound 25). 1.00 g compound 21 (2.64 mmole) was dissolved in 30 ml dry THF and 95 mg sodium hydride (3.97 mmole, 60% in mineral oil) was added at once. The reaction was stirred at room temperature under argon atmosphere during ½ h. After this period 570 µl diethylchlorophosphate was added and the reaction was further stirred for another 15 h. The reaction mixture was evaporated and the resulting residue was purified by flash chromatography (Acros Silicagel 0.060-0200 mm) using dichloromethane/ethyl acetate 93:7, affording compound 25 as a pale yellow oil (914 mg, 67% yield).

$^1$H-NMR: (500 MHz, CDCl$_3$): δ (ppm): 10.69 (s, 1H), 8.11 (d, 2.0 Hz, 1H), 7.83 (s, 1H), 7.72 (d, 8.3 Hz, 1H), 7.61 (dd, 2.1/8.3 Hz, 1H), 7.36 (d, 8.3 Hz, 1H), 7.31 (dd, 2.1/8.3 Hz, 1H), 4.26 (m, 4H), 2.75 (t, 7.6 Hz, 2H), 2.66 (t, 7.6 Hz, 2H), 1.65 (m, 4H), 1.34 (m, 14H), 0.89 (m, 6H).

IR (film): ν (cm$^{-1}$): 3389 (w, broad), 3188 (w), 2956 (w), 2929 (m), 2857 (w), 1688 (s), 1601 (m), 1493 (m), 1295 (m), 1217 (w), 1031 (s), 966 (w), 934 (w), 833 (w).

ES-MS (+) mode: 515.2 (M+H$^+$).

Synthesis of 2-(3H-4-oxo-6-n-pentyl-2-quinazolinyl)-4-n-pentylphenyl phosphate (compound 26). 358 mg compound 25 (694 µmole) was dissolved in 18 ml dichloromethane. 1.86 ml bis(trimethylsilyl) trifluoroacetic acid (6.94 mmole) was added and the reaction mixture was stirred at room temperature under argon for ½ h. The reaction was then cooled down to 0° C. and 795 µl trimethylsilyl iodide (5.56 mmole) was added drop wise. The reaction was stirred at 0° C. under argon atmosphere during 1 h. After this period 63 ml of a mixture acetonitrile/water/trifluoroacetic acid (10:5:3) was added and the reaction was stirred for 1 h at room temperature. The reaction mixture was evaporated and the resulting residue was purified by flash chromatography (Acros Silicagel 0.060-0.200 mm) using dichloromethane/methanol/formic acid 90:10:2. After addition of 100 ml toluene the function containing the product was concentrated affording compound 26 as orange crystals (238 mg, 58% yield).

$^1$H-NMR: (500 MHz, DMSO-d$_6$): δ (ppm): 7.94 (d, 1.9 Hz, 1H), 7.72 (dd, 1.9/8.4 Hz, 1H), 7.63 (d, 8.3 Hz, 1H), 7.55 (d, 1.9 Hz, 1H), 7.36 (dd, 2.1/8.3 Hz, 1H), 7.31 (d, 8.4 Hz, 1H), 2.74 (t, 7.5 Hz, 2H), 2.61 (t, 7.6 Hz, 2H), 1.62 (m, 4H), 1.32 (m, 8H), 0.87 (m, 6M).

IR (film): ν (cm$^{-1}$): 2930 (s, broad), 2857 (w), 1658 (s), 1495 (m), 1466 (w), 1329 (w), 1299 (w), 1201 (m), 947 (m), 841 (w), 719 (w), 624 (w), 526 (m).

ES-MS (+) mode: 457.4 (M+H$^+$).

Example 7

Enzymatic Tests in Mammalian and Plant Cells

Cells were electroporated in the presence of 10 µg pLNC-GUS and after 24 hours, compound 27 (10 mM stock in DMSO) was added to a final concentration of 10 µg/ml. Less than 5% of the cells had taken up the pLNCGUS plasmid. Cells electroporated in the absence of pLNCGUS only showed weak background fluorescence comparable with the non-fluorescent cells in the picture, as shown in FIG. 3.

compound 27

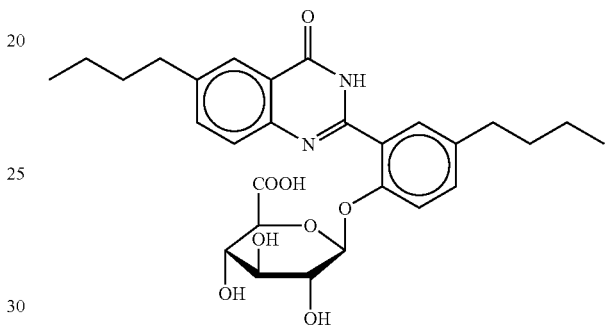

Example 8

Preparation of Naphthol-Quinazolinone Fluorophore 30

A naphtholic polyaromatic alkylated fluorophore can be prepared as follows: if instead of compound 18 (see example 4) 2-hydroxy-1-naphthoic acid is used, compound 30 can be synthesized the same way as described in example 4 for compound 21.

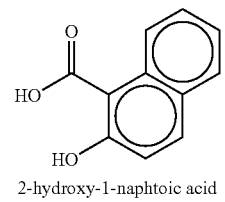

2-hydroxy-1-naphtoic acid

↓ HgCl$_2$/Zn
  HCl/H$_2$O/dioxane

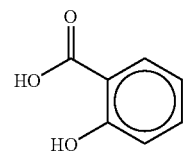

28

↓ ureum/H$_3$PO$_4$

-continued

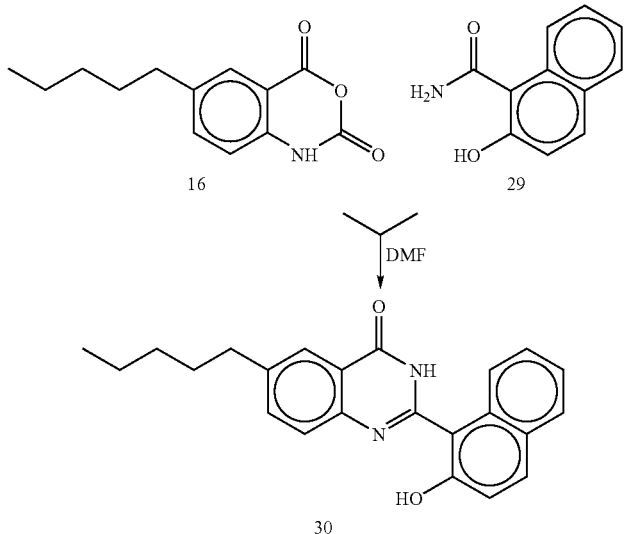

The invention claimed is:
1. An enzyme substrate of the formula (I):

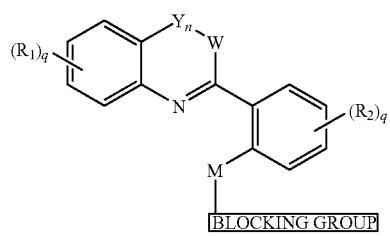

and biologically acceptable salt, and pro-reporter molecules thereof;
wherein
Y is C=O, and
n is 1 or 0;
W is —N($R_3$)—;
M is oxygen;
$R_1$ and $R_2$ are, each independently, hydrogen, halogen, nitro, azido, mercapto, sulfeno, sulfino, sulfo, cyano, amino, $R_4$—, $R_4$O—, $R_4$C(=Z)—, $R_4$X—C(=Z)—, $R_4$—C(=Z)—X—, $R_4$X—C(=Z)-Q-, $R_4$S—, $R_4$—S(=O)—, $R_4$—S(=O)—O—, $R_4$—S-(=O)$_2$-O—, $R_4$O—S—, $R_4$O—S—(=O)—, $R_4$O—S(=O)$_2$—, $R_4R_5$N—S(=O)—, $R_4R_5$N—S(=O)$_2$—, $R_4R_5$N—, [$R_4$—C(=Z)][$R_5$]N—, [$R_4$—C—(=Z)][$R_5$—C(=X)]N—, $R_4R_5$N—C(=Z)—, $R_4R_5$N—C(=Z)—X—, $R_4R_5$N—C(=Z)][$R_6$]N—, [$R_4R_5$N—C(=Z)][$R_6$—C(=X)]N—, [$R_4$—S(=O)][$R_5$]N—, [$R_4$—S(=O)$_2$][$R_5$]N—, ($R_4$X)($R_5$Q)P(=Z)—, ($R_4R_5$N)($R_6$X)P(=Z)—, ($R_4R_5$N)($R_6R_7$N)P(=Z)—, ($R_4$X)—($R_5$Q)P(=Z)—O—, ($R_4R_5$N)($R_6$X)P(=Z)—O—, ($R_4R_5$N)($R_6R_7$N)P(=Z)—O—, ($R_4$X)—($R_5$Q)P(=Z)—S—, ($R_4R_5$N)($R_6$X)P(=Z)—S—, ($R_4R_5$N)($R_6R_7$N)P(=Z)—S—, [($R_4$X)($R_5$Q)P(=Z)][$R_6$]N—, [($R_4R_5$N)($R_6$X)P(=Z)][$R_7$]N—, [($R_4R_5$N)($R_6R_7$N)P(=Z)][$R_8$]N—, ($R_4$)($R_5$X)P(=Z)—O—, ($R_4$)($R_5R_6$N)P(=Z)—O—, ($R_4$)($R_5$X)P(=Z)—S—, ($R_4$)($R_5R_6$N)P(=Z)—S—, [($R_4$)($R_5$X)—P(=Z)][$R_6$]N—, or [($R_4$)($R_5R_6$N)P(=Z)][$R_7$]N—;
wherein X, Z and Q are each independently oxygen or sulfur;
$R_3$ is $R_4$, $R_4$—C(=Z)—, $R_4$X—C(=Z)—, $R_4R_5$N—C(=Z)—, $R_4$O—S(=O)—, $R_4$O—S(=O)$_2$—, $R_4R_5$N—S(=O)—, $R_4R_5$N—S(=O)$_2$—, ($R_4$X)($R_5$Q)P(=Z)—, ($R_4R_5$N)($R_6$X)P(=Z)—, or ($R_4R_5$N)($R_6R_7$N)P(=Z)—;
wherein $R_4$, $R_5$, $R_6$, $R_7$ and $R_8$ are, each independently, hydrogen, $C_{1-8}$alkyl, $C_{2-8}$alkenyl, $C_{2-8}$alkynyl, $C_{3-7}$cycloalkyl, aryl, Het$^1$, or Het$^2$;
each q is independently 0, 1, 2, 3, or 4;
wherein any $C_{1-8}$alkyl, $C_{2-8}$alkenyl, $C_{2-8}$alkynyl or amino group, may be further mono, di-, or tri-substituted (if the valency allows it) with $C_{1-4}$alkoxy, $C_{1-4}$alkylcarbonyl, $C_{1-4}$alkoxycarbonyl, $C_{1-4}$alkylthio, $C_{1-4}$alkylsulfenyl, $C_{1-4}$alkylsulfinyl, $C_{1-4}$alkylsulfonyl, $C_{1-4}$alkylamino, halogen, nitro, azido, mercapto, sulfeno, sulfino, sulfo, cyano, amino, aryl, Het$^1$ or Het$^2$ substituents;
wherein Het$^1$ is a saturated or partially unsaturated monocyclic, bicyclic or tricyclic heterocycle having preferably 3 to 14 ring members, more preferably 5 to 10 ring members and more preferably 5 to 8 ring members, which contains one or more heteroatom ring members selected from nitrogen, oxygen or sulfur;
wherein Het$^2$ is an aromatic monocyclic, bicyclic or tricyclic heterocycle having preferably 5 to 14 ring members, more preferably 5 to 10 ring members and more preferably 5 to 6 ring members, which contains one or more heteroatom ring members selected from nitrogen, oxygen or sulfur;

wherein the BLOCKING GROUP is α-D-glucose, β-D-glucose, α-D-galactose, β-D-galactose, α-D-glucose, β-D-glucose, α-D-galactose, β-D-galactose, α-D-mannose, β-D-mannose, β-D-N-acetyl-glucosamine, β-D-glucuronic acid, β-D-fucose, α-L-fucose, α-L-iduronic acid, β-D-cellobiose, α-L-arabinose, β-D-xylose, α-D-N-acetyl-neuraminic acid (sialic acid), aryl esters of p-guanidino benzoic acid, aryl or alkyl phosphate monoesters, aryl sulfate monoesters, aryl phosphates-D-mannose, β-D-mannose, β-D-N-acetyl-glucosamine, β-D-glucuronic acid, β-D-fucose, α-L-fucose, α-L-iduronic acid, β-D-cellobiose, α-L-arabinose, β-D-xylose, α-D-N-acetyl-neuraminic acid (sialic acid), aryl esters of p-guanidino benzoic acid, aryl or alkyl phosphate monoesters, aryl sulfate monoesters, or aryl phosphates;

with the proviso that at least one $R_1$, $R_2$ and $R_3$ is a moiety with at least 4 carbons.

2. An enzyme substrate of the formula (I):

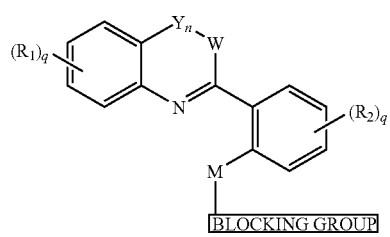

(I)

and biologically acceptable salts and pro-reporter molecules thereof;

wherein

Y is C=O, and n is 1 or 0;

W is —N($R_3$)—;

M is —O—;

each $R_1$ and each $R_2$ present in formula (I) are, independently, hydrogen, halogen, nitro, azido, mercapto, sulfeno, sulfino, sulfo, cyano, amino, $R_4$—, $R_4$O—, $R_4$—C(=Z)—, $R_4$X—C(=Z)—, $R_4$—C(=Z)—X—, $R_4$X—C(=Z)-Q-, $R_4$S—, $R_4$—S(=O)—, $R_4$—S(=O)$_2$—, $R_4$—S(=O)—O—, $R_4$—S(=O)$_2$—O—, $R_4$O—S—, $R_4$O—S(=O)—, $R_4$O—S(=O)$_2$—, $R_4R_5$N—S(=O)—, $R_4R_5$N—S(=O)$_2$—, $R_4R_5$N—, [$R_4$—C(=Z)][$R_5$]N—, [$R_4$—C(=Z)][$R_5$—C(=X)]N—, [$R_4$X—C(=Z)][$R_5$]N—, [$R_4$X—C(=Z)][$R_5$—C(=Q)]N—, $R_4R_5$N—C(=Z)—, $R_4R_5$N—C(=Z)—X—, [$R_4R_5$N—C(=Z)][$R_6$]N—, [$R_4R_5$N—C(=Z)][$R_6$C(=X)]N—, [$R_4$—S(=O)][$R_5$]N—, [$R_4$—S(=O)$_2$] [$R_5$]N—, ($R_4$X)($R_5$Q)P(=Z)—, ($R_4R_5$N)($R_6$X)P(=Z)—, ($R_4R_5$N)($R_6R_7$N)P(=Z)—, ($R_4$X)($R_5$Q)P(=Z)—O—, ($R_4R_5$N)($R_6$X)P(=Z)—O—, ($R_4R_5$N)($R_6R_7$N)P(=Z)—O—, ($R_4$X)—($R_5$Q)P(=Z)—S—, ($R_4R_5$N)($R_6$X)P(=Z)—S—, ($R_4R_5$N)($R_6R_7$N)P(=Z)—S—, [($R_4$X)($R_5$Q)P(=Z)][$R_6$]N—, [($R_4R_5$N)($R_6$X)P(=Z)][$R_7$]N—, [($R_4R_5$N)($R_6R_7$N)P(=Z)][$R_8$]N—, ($R_4$)($R_5$X)P(=Z)—O—, ($R_4$)($R_5R_6$N)P(=Z)—O—, ($R_4$)($R_5$X)P(=Z)—S—, ($R_4$)($R_5R_6$N)P(=Z)—S—, [($R_4$)($R_5$X)P(=Z)][$R_6$]N—, or [($R_4$)($R_5R_6$N)P—(=Z)][$R_7$]N—;

wherein X, Z and Q are each, independently, O or S;

$R_3$ is $R_4$, $R_4$—C(=Z)—, $R_4$X—C(=Z)—, $R_4R_5$N—C(=Z)—, $R_4$O—S(=O)—, $R_4$O—S(=O)$_2$—, $R_4R_5$N—S(=O)—, $R_4R_5$N—S(=O)$_2$—, ($R_4$X)($R_5$Q)P(=Z)—, ($R_4R_5$N)($R_6$X)—P—(=Z)—, or ($R_4R_5$N)($R_6R_7$N)P(=Z)—;

wherein $R_4$, $R_5$, $R_6$, $R_7$ and $R_8$ are each, independently, hydrogen, $C_{1-8}$alkyl, $C_{2-8}$alkenyl, $C_{2-8}$alkynyl, $C_{3-7}$cycloalkyl, aryl, Het$^1$, or Het$^2$;

wherein Het$^1$ is a saturated or partially unsaturated monocyclic, bicyclic or tricyclic heterocycle having preferably 3 to 14 ring members, more preferably 5 to 10 ring members and more preferably 5 to 8 ring members, which contains one or more heteroatom ring members selected from nitrogen, oxygen or sulfur;

wherein Het$^2$ is an aromatic monocyclic, bicyclic or tricyclic heterocycle having preferably 5 to 14 ring members, more preferably 5 to 10 ring members and more preferably 5 to 6 ring members, which contains one or more heteroatom ring members selected from nitrogen, oxygen or sulfur;

each q present in formula (I) is, independently, 0, 1, 2, 3, or 4;

wherein any $C_{1-8}$alkyl, $C_{2-8}$alkenyl, $C_{2-8}$alkynyl or amino group, may be further mono, di-, or tri-substituted (if the valency allows it) with $C_{1-4}$alkoxy, $C_{1-4}$alkylcarbonyl, $C_{1-4}$ alkoxycarbonyl, $C_{1-4}$alkylthio, $C_{1-4}$alkylsulfenyl, $C_{1-4}$alkylsulfinyl, $C_{1-4}$alkylsulfonyl, $C_{1-4}$ alkylamino, halogen, nitro, azido, mercapto, sulfeno, sulfino, sulfo, cyano, amino, aryl, Het$^1$ or Het$^2$ substituents;

wherein the BLOCKING GROUP is α-D-glucose, β-D-glucose, α-D-galactose, β-D-galactose, α-D-glucose, β-D-glucose, α-D-galactose, β-D-galactose, α-D-mannose, β-D-mannose, β-D-N-acetyl-glucosamine, β-D-glucuronic acid, β-D-fucose, α-L-fucose, α-L-iduronic acid, β-D-cellobiose, α-L-arabinose, β-D-xylose, α-D-N-acetyl-neuraminic acid (sialic acid), aryl esters of p-guanidino benzoic acid, aryl or alkyl phosphate monoesters, aryl sulfate monoesters, aryl phosphates-D-mannose, β-D-mannose, β-D-N-acetyl-glucosamine, β-D-glucuronic acid, β-D-fucose, α-L-fucose, α-L-iduronic acid, β-D-cellobiose, α-L-arabinose, β-D-xylose, α-D-N-acetyl-neuraminic acid (sialic acid), aryl esters of p-guanidino benzoic acid, aryl or alkyl phosphate monoesters, aryl sulfate monoesters, or aryl phosphates;

with the proviso that at least one of $R_1$, $R_2$ and $R_3$ is $C_{4-8}$alkyl, $C_{4-8}$alkenyl, or $C_{4-8}$alkynyl.

3. A substrate according to claim 1, wherein at least one of $R_1$, $R_2$ and $R_3$ is independently chosen from the group consisting of straight and branched butyl, pentyl, hexyl, heptyl, or octyl.

4. A substrate according to claim 1, wherein W is —N($R_3$)—, Y is —C(=O)—, and n is 1 and having the formula (II)

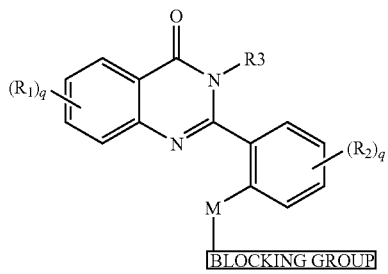
(II)
wherein M, $R_1$, $R_2$, $R_3$, q and the BLOCKING GROUP are as defined as in claim 1.
5. A substrate according to claim 1, having the formula (III)
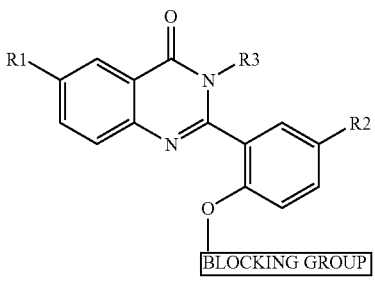
(III)
wherein $R_1$, $R_2$, $R_3$, and the BLOCKING GROUP are as defined as in claim 1.
* * * * *